US012303246B2

(12) United States Patent
Tu et al.

(10) Patent No.: US 12,303,246 B2
(45) Date of Patent: May 20, 2025

(54) METHODS AND SYSTEMS FOR PRECISE QUANTIFICATION OF HUMAN SENSORY CORTICAL AREAS

(71) Applicants: Yanshuai Tu, Mesa, AZ (US); Yalin Wang, Tempe, AZ (US); Zhong-Lin Lu, New York, NY (US)

(72) Inventors: Yanshuai Tu, Mesa, AZ (US); Yalin Wang, Tempe, AZ (US); Zhong-Lin Lu, New York, NY (US)

(73) Assignees: ARIZONA BOARD OF REGENTS ON BEHALF OF ARIZONA STATE UNIVERSITY, Scottsdale, AZ (US); NEW YORK UNIVERSITY, New York, NY (US)

( * ) Notice: Subject to any disclaimer, the term of this patent is extended or adjusted under 35 U.S.C. 154(b) by 950 days.

(21) Appl. No.: 17/221,507

(22) Filed: Apr. 2, 2021

(65) Prior Publication Data
US 2021/0307610 A1    Oct. 7, 2021

Related U.S. Application Data

(60) Provisional application No. 63/004,721, filed on Apr. 3, 2020.

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0042* (2013.01); *G01R 33/4806* (2013.01);
(Continued)

(58) Field of Classification Search
CPC ..... G01R 33/4806; G06T 7/11; G06T 7/0012; A61B 5/4005; A61B 5/4064
See application file for complete search history.

(56) References Cited

U.S. PATENT DOCUMENTS

2012/0265050 A1* 10/2012 Wang ..................... A61B 6/485
                                                                                600/411
2016/0292847 A1* 10/2016 Liu ........................... G06T 7/68
(Continued)

OTHER PUBLICATIONS

Lui et al, Texture Map and Video Compression Using Beltrami Representation, 2013 (Year: 2013).*
(Continued)

*Primary Examiner* — Jeffrey G Hoekstra
*Assistant Examiner* — Gabriel Victor Popescu
(74) *Attorney, Agent, or Firm* — Snell & Wilmer L.L.P.

(57) ABSTRACT

A sensory mapping method for a human brain is disclosed. The method includes the steps of flattening the cortical surface of the human brain, projecting functional imaging data onto the flattened surface, smoothing the functional imaging data, generating a sensory map, registering sensory maps across individuals and analyzing the maps in the common space. The flattening utilizes a conformal parametrization method. The smoothing utilizes a topological smoothing method that utilizes a diffeomorphic smoother. The registering is diffeomorphic. The sensory mapping method may further include a step of processing the functional imaging data to produce topological results.

9 Claims, 19 Drawing Sheets

(a) Harmonic Map    (b) Cortical Surface    (c) Conformal Map

(51) Int. Cl.
  *G01R 33/48*  (2006.01)
  *G01R 33/56*  (2006.01)
  *G06T 3/04*  (2024.01)
  *G06T 3/06*  (2024.01)
  *G06T 3/14*  (2024.01)
  *G06T 7/11*  (2017.01)
  *G06T 7/70*  (2017.01)

(52) U.S. Cl.
  CPC ............ *G01R 33/5608* (2013.01); *G06T 3/04* (2024.01); *G06T 3/06* (2024.01); *G06T 3/14* (2024.01); *G06T 7/11* (2017.01); *G06T 7/70* (2017.01); *A61B 2576/026* (2013.01); *G06T 2207/10088* (2013.01); *G06T 2207/30016* (2013.01)

(56) References Cited

U.S. PATENT DOCUMENTS

| | | | | |
|---|---|---|---|---|
| 2016/0343127 | A1* | 11/2016 | Miller | A61B 5/055 |
| 2016/0350979 | A1* | 12/2016 | Zeng | G06T 7/0012 |
| 2019/0120919 | A1* | 4/2019 | Saggar | A61B 5/165 |
| 2019/0192039 | A1* | 6/2019 | Ta | A61B 5/4064 |
| 2019/0205766 | A1* | 7/2019 | Krebs | G06T 7/0012 |
| 2020/0286225 | A1* | 9/2020 | Ben-Haim | G06T 7/0012 |

OTHER PUBLICATIONS

Qiu, Smooth Functional and Structural Maps on the Neocortex Via Orthonormal Bases of the Laplace-Beltrami Operator, 2006, IEEE (Year: 2006).*
Robert F. Dougherty, Volker M. Koch, Alyssa A. Brewer, Bernd Fischer, Jan. Modersitzki, and Brian A. Wandell, "Visual field representations and locations of visual areas v1/2/3 in human visual cortex," Journal of Vision, vol. 3, No. 10, pp. 586-598, Oct. 2003.
Serge O. Dumoulin and Brian A. Wandell, "Population receptive field estimates in human visual cortex," NeuroImage, vol. 39, No. 2, pp. 647-660, Jan. 2008.
Ivan Alvarez, Benjamin de Haas, Chris A. Clark, Geraint Rees, and D. Samuel Schwarzkopf, "Comparing different stimulus configurations for population receptive field mapping in human fMRI," Frontiers in Human Neuroscience, vol. 9, Feb. 2015.
Jonathan W Peirce, "Generating stimuli for neuroscience using PsychoPy," Frontiers in Neuroinformatics, vol. 2, pp. 10, Jan. 2008.
M. I. Sereno, S Pitzalis, and A Martinez, "Mapping of Contralateral Space in Retinotopic Coordinates by a Parietal Cortical Area in Humans," Science, vol. 294, No. 5545, pp. 1350-1354, Nov. 2001.
Jonathan C. Horton, "The Representation of the Visual Field in Human Striate Cortex," Archives of Ophthalmology, vol. 109, No. 6, pp. 816, Jun. 1991.
J. Warnking, M. Dojat, A. Gu'erin-Dugu'e, C. Delon-Martin, S. Olympieff, N. Richard, A. Ch'ehikian, and C. Segebarth, "fMRI Retinotopic Mapping—Step by Step," NeuroImage, vol. 17, No. 4, pp. 1665-1683, Dec. 2002.
Nicholas V. Swindale, Doron Shoham, Amiram Grinvald, Tobias Bonhoeffer, and Mark Hübener, "Visual cortex maps are optimized for uniform coverage," Nature Neuroscience, vol. 3, No. 8, pp. 822-826, Aug. 2000.
Matthew F. Glasser, Stamatios N. Sotiropoulos, J. Anthony Wilson, Timothy S. Coalson, Bruce Fischl, Jesper L. Andersson, Junqian Xu, Saad Jbabdi, Matthew Webster, Jonathan R. Polimeni, David C. Van Essen, and Mark Jenkinson, "The minimal preprocessing pipelines for the Human Connectome Project," NeuroImage, vol. 80, pp. 105-124, Oct. 2013.
M. Sereno, A. Dale, J. Reppas, K. Kwong, J. Belliveau, T. Brady, B. Rosen, and R. Tootell, "Borders of multiple visual areas in humans revealed by functional magnetic resonance imaging," Science, vol. 268, No. 5212, pp. 889-893, May 1995.
Noah C Benson and JonathanWinawer, "Bayesian analysis of retinotopic maps," eLife, vol. 7, Dec. 2018.
Eric L. Schwartz, "Computational anatomy and functional architecture of striate cortex: a spatial mapping approach to perceptual coding," Vision Research, vol. 20, No. 8, pp. 645-669, Jan. 1980.
Daniel L Adams and Jonathan C Horton, "A precise retinotopic map of primate striate cortex generated from the representation of angioscotomas.," The Journal of neuroscience : the official journal of the Society for Neuroscience, vol. 23, No. 9, pp. 3771-3789, May 2003.
Noah C. Benson and Others, "The Human Connectome Project 7 Tesla retinotopy dataset: Description and population receptive field analysis," Journal of Vision, vol. 18, No. 13, pp. 1-22, Dec. 2018.
B.A. Wandell, J. Winawer, and K.N. Kay, "Computational Modeling of Responses in Human Visual Cortex," in Brain Mapping, pp. 651-659. Elsevier, Feb. 2015.
Mark M. Schira, Christopher W. Tyler, Branka Spehar, and Michael Breakspear, "Modeling Magnification and Anisotropy in the Primate Foveal Confluence," PLoS Computational Biology, vol. 6, No. 1, pp. e1000651, Jan. 2010.
Duyan Ta, Jie Shi, Brian Barton, Alyssa Brewer, Zhong-Lin Lu, and YalinWang, "Characterizing human retinotopic mapping with conformal geometry: a preliminary study," in Medical Imaging 2014: Image Processing, Sebastien Ourselin and Martin A. Styner, Eds., Mar. 2014, vol. 9034, p. 90342A.
Dimas Mart'nez, Luiz Velho, and Paulo C. Carvalho, "Computing geodesics on triangular meshes," Computers and Graphics (Pergamon), vol. 29, No. 5, pp. 667-675, Oct. 2005.
Lok Ming Lui, Ka Chun Lam, Tsz Wai Wong, and Xianfeng Gu, "Texture map and video compression using Beltrami representation," SIAM Journal on Imaging Sciences, vol. 6, No. 4, pp. 1880-1902, Jan. 2013.
Ka Chun Lam and Lok Ming Lui, "Landmark and intensity-based registration with large deformations via quasi-conformal maps," SIAM Journal on Imaging Sciences, vol. 7, No. 4, pp. 2364-2392, Jan. 2014.
Paul H.C. Eilers, "A perfect smoother," AnalyticalChemistry, vol. 75, No. 14, pp. 3631-3636, Jul. 2003.
Brian A. Wandell and Jonathan Winawer, "Imaging retinotopic maps in the human brain," Vision Research, vol. 51, No. 7, pp. 718-737, Apr. 2011.
F. Vasseur, C. Delon-Martin, C. Bordier, J. Warnking, L. Lamalle, C. Segebarth, and M. Dojat, "fMRI retinotopic mapping at 3 T: Benefits gained from correcting the spatial distortions due to static field inhomogeneity," Journal of Vision, vol. 10, No. 12, pp. 30-30, Oct. 2010.
B Fischl, M I Sereno, and A M Dale, "Cortical surface-based analysis. II: Inflation, flattening, and a surfacebased coordinate system," Neuroimage, vol. 9, No. 2, pp. 195-207, Feb. 1999.
Stephen M. Smith and Others, "Advances in functional and structural MR image analysis and implementation as FSL," NeuroImage, vol. 23, No. SUPPL. 1, pp. S208-S219, Jan. 2004.
David W Shattuck and Richard M Leahy, "BrainSuite: an automated cortical surface identification tool.," Medical image analysis, vol. 6, No. 2, pp. 129-142, Jun. 2002.
Rainer Sprengel, Karl Rohr, and H. Siegfried Stiehl, "Thin-plate spline approximation for image registration," in Annual International Conference of the IEEE Engineering in Medicine and Biology—Proceedings. 1996, vol. 3, pp. 1190-1191, IEEE.
Tom Vercauteren, Xavier Pennec, Aymeric Perchant, and Nicholas Ayache, "Diffeomorphic demons: efficient non-parametric image registration.," NeuroImage, vol. 45, No. 1 Suppl, pp. S61-S72, Mar. 2009.
M. Faisal Beg, Michael I. Miller, Alain Trouv'e, and Laurent Younes, "Computing large deformation metric mappings via geodesic flows of diffeomorphisms," International Journal of Computer Vision, vol. 61, No. 2, pp. 139-157, Feb. 2005.

\* cited by examiner

METHODS AND SYSTEMS FOR PRECISE QUANTIFICATION OF HUMAN SENSORY CORTICAL AREAS

CROSS REFERENCE TO RELATED APPLICATIONS

This application claims priority to and the benefit of U.S. Provisional Patent Application No. 63/004,721, filed on Apr. 3, 2020 and entitled "Methods and Systems for Precise Quantification of Human Sensory Cortical Areas," which is hereby incorporated by reference in its entirety (but excepting any subject matter disclaimers or disavowals, and except to the extent that the incorporated material is inconsistent with the express disclosure herein, in which case the language in this disclosure shall control).

FEDERALLY SPONSORED RESEARCH OR DEVELOPMENT

This invention was made with government support under 1413417 and 1412722 awarded by the National Science Foundation. The government has certain rights in the invention.

TECHNICAL FIELD

The present disclosure relates to imaging, and in particular to techniques for imaging brain structure and activity.

SUMMARY

Methods and systems for precise quantification of human sensory cortical areas are disclosed. In an exemplary embodiment, a sensory mapping method for a human brain comprises flattening the cortical surface of the human brain, projecting functional imaging data onto the flattened surface, smoothing the functional imaging data or processing the functional imaging data to produce topological results, generating the sensory map, registering sensory maps across individuals, and analyzing the maps in the common space. The sensory mapping method may further comprise rendering the sensory map with an image of stimuli that activate the cortical surface.

The flattening may comprise a conformal parametrization method. The flattening may comprise applying harmonic mapping to a unit disk and refining repetitively parametric coordinate for each point on a parameter domain to produce conformal mapping.

The smoothing may comprise a topological smoothing method that utilizes a diffeomorphic smoother. The smoothing may comprise applying Beltrami coefficient to quantify diffeomorphism and modeling the smoothing in an optimization framework.

The processing may comprise a topology-preserving cortical surface segmentation method. The processing may comprise segmenting the cortical surface of the human brain by preserving the prior connectivity pattern of the cortical surface areas, decoding the functional imaging data based on at least one topological condition within each cortical area, and repeating the segmentation and decoding.

The registering may be diffeomorphic. The registering may comprise a method that aligns a human brain sensory map of an individual to a predefined template.

In another exemplary embodiment, a sensory mapping method for a human brain comprises flattening the cortical surface of the human brain, projecting functional imaging data onto the flattened surface, processing the functional imaging data to produce topological results, and generating a sensory map. The processing may comprise a topology-preserving cortical surface segmentation method.

The contents of this section are intended as a simplified introduction to the disclosure, and are not intended to be utilized to limit the scope of any claim.

BRIEF DESCRIPTION OF THE DRAWINGS

With reference to the following description and accompanying drawings.

DETAILED DESCRIPTION

Figure 1:
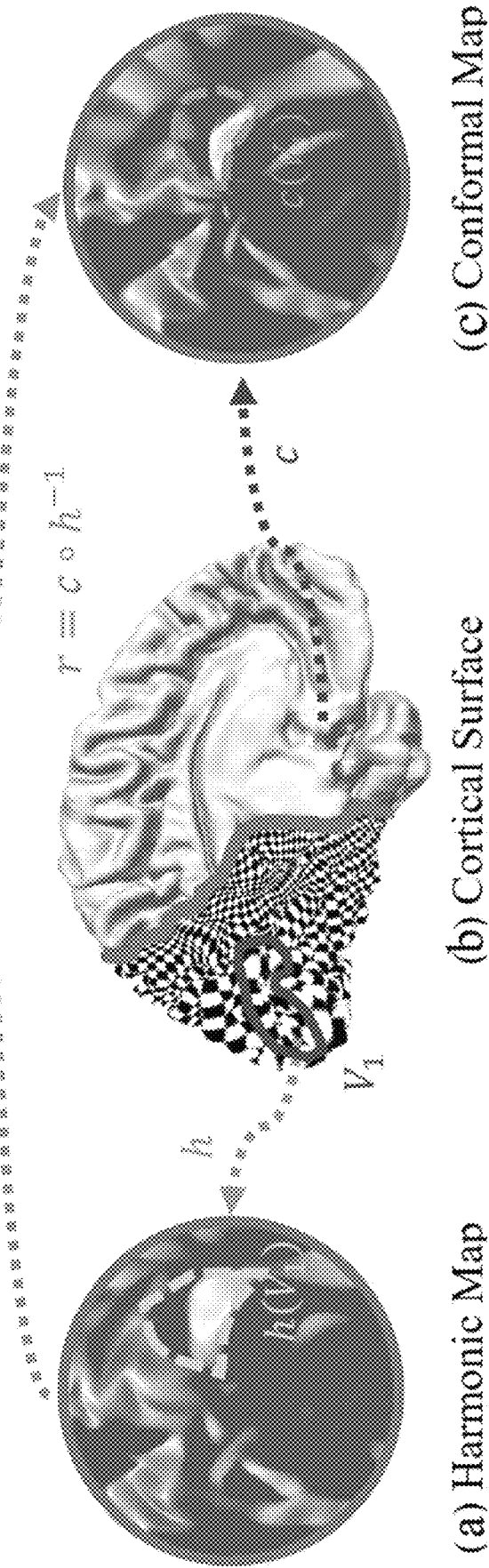
FIG. 1 illustrates a conformal parameterization process in accordance with various exemplary embodiments: (a) harmonic map of the region of interest; (b) cortical surface and region of interest; the checker-board texture inferred from the conformal map is applied on the region of interest; and (c) the resulting conformal map of the region of interest.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques and components for mathematical processes, transforms, mapping, smoothing, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in exemplary methods and systems for imaging and/or components thereof.

Sensory maps of the human brain are of great scientific interest and could have important medical applications. fMRI makes it possible to define the sensory maps for an individual in vivo. However, due to the low signal-noise ratio and low spatial resolution of fMRI, the sensory maps are usually noisy and don't preserve topology.

In particular, in clinical settings, doctors require quantitative scores. The current mapping methods of the sensory areas of the human brain can only generate qualitative maps with high uncertainty. To address these shortcomings of prior approaches, exemplary embodiments provide smoothing tools, topology correction tools, quantification tools, and multi-subject alignment tools to generate a complete quantitative description of the maps. The quantitative scores are desirable, for example in connection with disease diagnosis and prognosis.

The sensory areas of the brain, including the auditory cortex, visual cortex, and so forth, contain topographical representations of the sensory space. Functional magnetic resonance imaging (fMRI) signals have produced subject-specific cortical maps. However, such maps are noisy, incomplete, and even contradict neurophysiological results. In contrast, the methods and systems in this disclosure can reduce the noise, fix topology violations, and quantify the properties of the maps across time and/or individuals. In particular, exemplary systems and methods can precisely smooth, register, and quantify sensory maps of the human brain. The methods and systems can be used to quantify properties of the sensory areas of the human brain that are associated with normal and abnormal development, aging, and diseases related to sensory processing.

An exemplary method for quantification of a sensory map comprises: (1) flattening the cortical surface; (2) projecting the functional imaging data onto the flattened surface; (3) smoothing the functional imaging data or processing the functional imaging data to produce topological results; (4) generating the sensory map; (5) registering sensory maps across individuals; (6) analyzing the maps in the common space. The sensory map may be a retinotopic map.

With reference now to FIGS. 1 through 18, in accordance with various exemplary embodiments, exemplary methods utilize concepts from computational geometry and provide techniques to reduce noise, fix topology violations, and precisely quantify the properties of the sensory maps. In an exemplary embodiment, the disclosed systems and methods may be applied to visual retinotopic maps with excellent results. However, all practical applications of principles of the present disclosure are contemplated herein.

Figure 2:
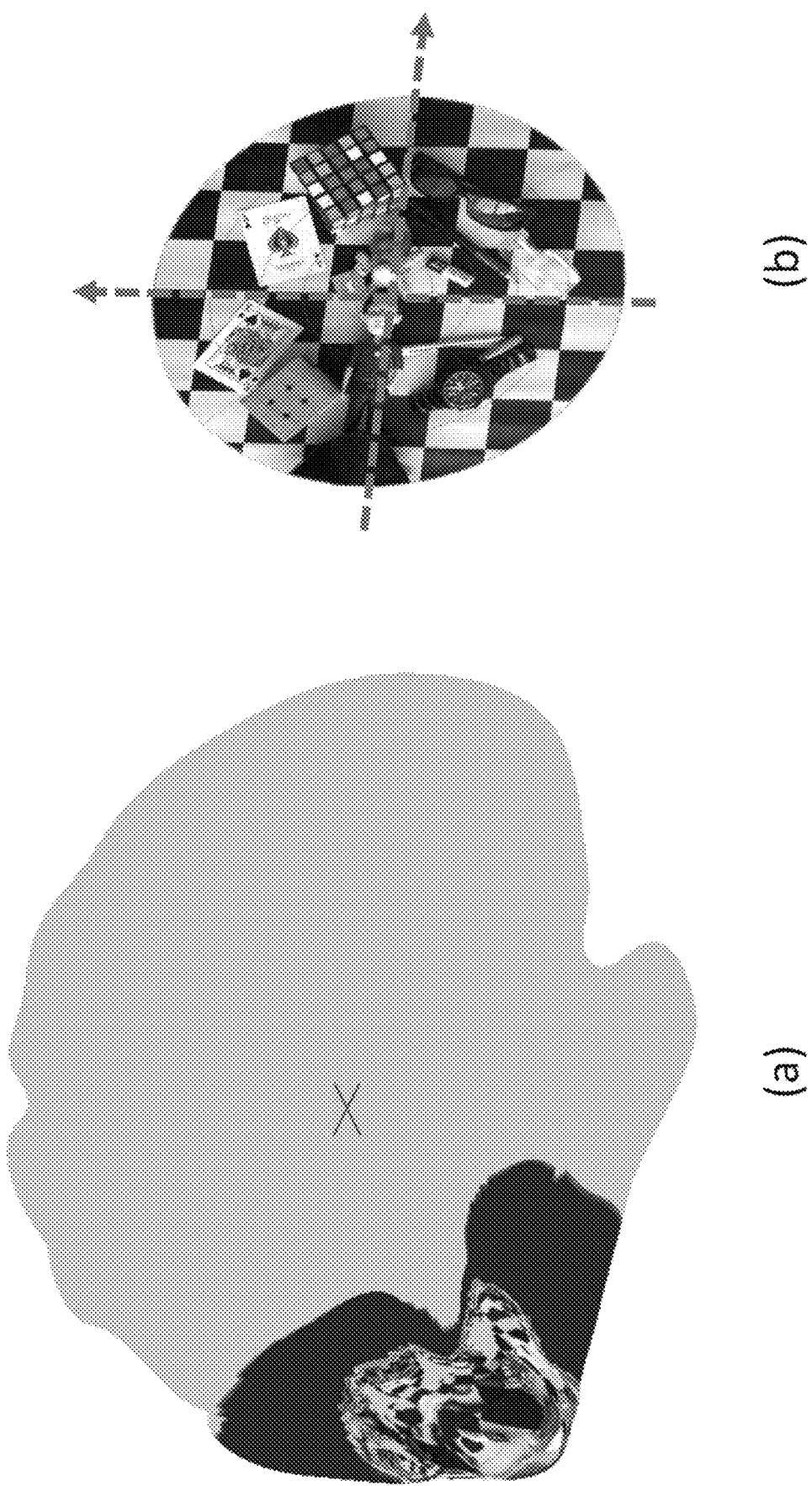
FIG. 2 illustrates a texture map between visual field image and visual cortex in accordance with various exemplary embodiments.

FIGS. 1-2 illustrate methods and systems for flattening a cortical surface. FIGS. 3-8 illustrate methods and systems for smoothing the functional imaging data. FIGS. 9-13 illustrate methods and systems for processing the functional imaging data to produce topological results. FIGS. 13-18 illustrate methods and systems for registering sensory maps.

Exemplary systems and methods may use a conformal mapping method together with a geodesic disk to reduce angle distortion and geodesic distortion. Exemplary systems and methods may correct topology violations and perform topology-preserving smoothing. Exemplary systems and methods may reduce angle distortion as well as geodesic distortion and produce high quality mapping. Exemplary systems and methods may provide utilities to register or align sensory maps across subjects based on both structural and functional MRI data. The exemplary systems and methods disclosed herein may be integrated to allow the quantification of human brain sensory maps.

In an exemplary embodiment, in a sensory mapping method, visual cortical surfaces are conformally mapped to a topological disk on which local geometry structures are well preserved. Then retinotopy data are smoothed to ensure that topology is preserved on the maps. Specifically, the Beltrami coefficient is adopted as the metric of topology, and a topology-preserving smoothing formulation is solved efficiently. It is believed that the disclosed method may be the first method that can smooth the retinotopic maps and fix topology violations. Thereafter, quantitative properties of the maps, e.g., cortical magnification factor, can be measured precisely using differential geometry tools on the smoothed cortical maps.

In addition to use for analyzing the sensory maps of individual subjects, principles of the present disclosure also provide the capability to better align and analyze sensory maps across time and/or subjects. By considering the intrinsic structure in the sensory maps, exemplary methods can achieve better cortical registration across subjects.

Exemplary systems and methods make it possible to precisely quantify sensory maps of individuals and further improve the quality of sensory maps with data from multiple individuals. Although various exemplary embodiments disclosed herein are discussed in the context of visual retinotopic maps, those skilled in the art will appreciate that principles of the present disclosure can also be applied to all the other sensory areas, including the auditory cortex, somatosensory cortex, and olfactory cortex.

Methods and Systems for Flattening a Cortical Surface

As shown in FIG. 1, an exemplary method is disclosed herein for conformal disk parameterization, c: M→D, to flatten the cortical surface patch M to the disk domain D, the check-board region in and the disk in FIG. 1.

To achieve quality conformal mapping results, a new algorithm is introduced to achieve conformal mapping of the V1 retinotopic map on the unit disk D. First, the harmonic mapping is applied to the unit disk as the initial mapping. FIG. 1(a) illustrates harmonic mapping of a region of interest whose location in the cortical surface is labeled in FIG. 1(b). This produces the result that the boundary of M is on the boundary of the D. Second, the conformality of the patch is iteratively optimized until the BC within V1 is within the predefined error $|\mu|_\infty < \varepsilon$, as shown in FIG. 1(c).

Harmonic Maps

The harmonic map h: M→D can be found by minimizing the following energy.

$$E(h) = \int_M |\nabla h|_2 dv_M$$

The harmonic map for disk-like surfaces h: M→D can be found by setting $\nabla E(h)=0$, which yields the Laplace equation $$\Delta h(u)_M = 0$$

$$h/\partial M = g$$

where $\Delta$ is the Laplacian operator and g: $\partial M \to \partial G$ can be given by the arc length parameterization.

In the discrete case, the Laplace equation is a sparse linear system, written as $L^h h = 0$. The matrix element $Lh/i,j$ is $$L_{i,j}^h = \begin{cases} \sum_{[u_i, u_j, u_k] \in N(i)} \frac{(As_i) \cdot s_i}{|[u_i, u_j, u_k]|}, & \text{if } i \neq j \\ -\sum_{k \neq i} L_{i,k}, & \text{if } i = j \\ 0, & \text{otherwise.} \end{cases}$$

Here, the boundary vertices are set by their boundary length. Each vertex $\{v_i\}_{i=0}^{n-1}$ is mapped to the unit circle according to the ratio of the edge lengths along the boundary loop. The harmonic map h is efficiently obtained by solving the linear system.

Optimizing Conformality in the Primary Visual Cortex (V1)

After the harmonic mapping is achieved, the parametric coordinate is iteratively refined for each point on the parameter domain to achieve conformal mapping in the primary visual cortex (V1). Let r be the desired refinement map, such that the result r is conformal mapping to 3D cortical surface in V1. The mapping that this method is seeking $r = c \cdot h^{-1}$ is illustrated in FIG. 1 (a)-(c). As described above, if there is the Beltrami coefficient $\mu_r$ of r, r can be reconstructed. If c is conformal, the Beltrami coefficient of the composite map is $\mu_r = h^{-1}$. Since h is given, its inverse $h^{-1}$ can be computed. To compute the Beltrami coefficients for the inverse harmonic map in the discrete case, i.e., $h^{-1}$: D→M between the corresponding triangular faces, the first step is to use piecewise rigid motion transformation R to translate each triangular face of M onto $R^2$. Then the next step is to compute the Beltrami coefficient, $\mu_{R \cdot h^{-1}}$, of the map $R \cdot h^{-1}$. Since rigid motions are conformal, the resulting Beltrami coefficient $\mu_{R \cdot h^{-1}}$ equals $\mu_{h^{-1}}$. With the defined $\mu_r$ the next step is to compute a new mapping r and achieve the desired conformality. Numerically, to achieve the best quality, the refinement is repeated until the mapping is conformal, i.e., pc falls below a predefined error bound $^\varepsilon\mu_r$, $\|\mu_r\|_\infty \leq ^\varepsilon\mu_r$.

Because a goal is to achieve a conformal parameterization of the primary visual cortical surface (V1), $\mu_r = \mu_{h-1}$ is set for the faces in the V1 area. For other parts, $\mu_r$ is kept unchanged. The conformal procedure for the primary visual cortex (V1) is summarized in the following Algorithm 1. Finally, an observer-wise Mobius transformation is applied on the disk, a conformal transformation with analytical scaling and rotating, to eliminate conformal mapping ambiguity and roughly align the visual regions between observers.

Once the conformal parameterization is obtained, the next step is V1's retinotopic mapping from the parametric disk to the visual field. More specifically, the 2D map is $f\_r$: $c(V1) \to D$, from the parametric domain of V1 cortex to the visual field. With the bijective conformal parameterization c, the retinotopic mapping can be evaluated through a planar-to-planar function $f: D_{V1} \to D$ such that $D_{V1} = c(V1)$ and $f = f_r \cdot c^{-1}$.

Algorithm 1: Conformal parametrization of the visual cortex.

Input: Cut patch $M = (P_M, E_M, F_M)$, where $P_M = \{P_i\}$ is the mesh vertex set; vertex indices $I_P$ and face indices $I_F$ for the primary visual cortex respectively, and a tolerance $^\varepsilon\mu_r$ Output: Conformal parametric coordinates $\{u_i | i \in I_P\}$
1 begin
2 Compute the harmonic parametric $h = \{h_i | P_i \in P_M\}$;
3 Initialize $u_i \leftarrow h_i$, $\delta\mu \leftarrow \infty$;
4 Compute the Beltrami coefficient $\{\mu_i | f_i \in F_M\}$ for the inverse map $u^{-1}$
5 while $\delta\mu > ^\varepsilon\mu_r$ do
6 Change BC to zero in visual cortex, i.e., $\mu^0_i = 0$, $\forall i \in I_F$, and $\mu^0_i = \mu_i$, $\forall i \in I_F$;
7 Fix the boundary points and compute the refined coordinate $\{ui | Pi \in P_M\}$
8 Compute the Beltrami coefficient $\{\mu_i | f_i \in F_M\}$ for the inverse map $u^{-1}$
9 Update maximal BC in V1, by $\delta\mu \leftarrow \max|\mu i|: i \in I_F$
10 end
11 return $\{u_i\}$
12 end Illustrative Visualization of the Retinotopic Map Once a complete retinotopic map is processed by the method described herein, the following method provides an intuitive illustration of the perception centers by texture mapping, as shown in FIG. 2. This texture map becomes meaningful with the smooth and topological retinotopic map. Specifically, the visual coordinate for each visual cortex is first computed, as shown in FIG. 2a. Then the next step is to interpret visual coordinate for point within the triangular face with the utilities of OpenGL. The final step is to render the cortical surface with the visual image shown in FIG. 2b. This method can easily be used to check, invest, and verify discoveries relates to the retinotopic map.

Methods and Systems for Smoothing the Functional Imaging Data

Summary

Retinotopic mapping, the mapping of visual input on the retina to cortical neurons, is an important topic in vision science. Typically, cortical neurons are related to visual input on the retina using functional magnetic resonance imaging (fMRI) of cortical responses to slowly moving visual stimuli on the retina. Although it is known from neurophysiology studies that retinotopic mapping is locally diffeomorphic (i.e., smooth, differentiable, and invertible) within each local area, the retinotopic maps from fMRI are not diffeomorphic, especially near the fovea, because of the low signal-noise ratio of fMRI. The present disclosure discloses a mathematical model that produces diffeomorphic retinotopic mapping from fMRI data. In an exemplary embodiment, the present disclosure adopts a geometry concept, the Beltrami coefficient, as the tool to define diffeomorphism, and models the problem in an optimization framework. Efficient numerical methods are applied to produce the model. Experimental results with both synthetic and real retinotopy data demonstrate that the method disclosed herein is superior to conventional smoothing methods.

Introduction

Almost half of the human cerebral cortex is dedicated to visual processing. Identifying and analyzing visual areas of the human brain is an important topic in vision science and neurobiology. Retinotopic mapping via functional magnetic resonance imaging (fMRI) provides a noninvasive way of defining the location and size of receptive filed of populations of visual neurons on the retina. Typically, cortical neurons are related to visual input on the retina using fMRI of cortical responses to slowly moving visual stimuli on the retina. The visual stimulus is carefully designed so that the stimulus pattern is unique with respect to each retinal location. By recording and analyzing the fMRI signals at each cortical location, one can decode the retinal visual input coordinate that generates such fMRI signals. Previous studies have revealed that much of the visual cortex is organized into visual regions (e.g., V1, V2) with a retinotopic map in each region. It is known from neurophysiology studies that retinotopic mapping is topology preserving (i.e., local neighborhood relationships are maintained) and diffeomorphic (i.e., smooth, differentiable, and invertible) within each visual area. However, the decoded visual coordinates from fMRI retinotopic mapping studies are not diffeomorphic or topological preserving. One reason is that the signal-noise ratio and spatial resolution of fMRI signals are low. Another reason is that the decoding process largely deciphers the fMRI signal point by point without considering the local smoothness, although Gaussian spatial smoother has been applied to fMRI signal processing.

Spatial smoothing was previously conducted on retinotopic maps to perform automatic delineation of visual regions. However, the smoothing is applied to the visual coordinates one dimension at a time, e.g., the x and y visual coordinates separately. There is no guarantee of diffeomorphism. Another approach is registering the noisy retinotopic maps to a diffeomorphic template and assigning the template retinotopic coordinates after registration. It relies on diffeomorphic registration of two surfaces, which is difficult to achieve. Even if the registration issue can be solved, how to define the right template will remain a big problem. Therefore, there is a need to solve the smoothing issue.

In an exemplary embodiment, a method is disclosed that applies the Beltrami coefficient to quantify the diffeomorphism as well as angle deviation. It is known that retinotopic mappings preserve angles to a considerable extent. The method further models the smoothing process as an optimization procedure with diffeomorphic constraints and elaborates the numerical steps to solve the optimization problem. The algorithm was tested on a synthetic dataset and a real dataset. The synthetic data is generated using an ideal retinotopic mapping model (ground truth) with added noise. The application of the method to the synthetic data generates diffeomorphic results without any large deviations, while other methods violate the condition. The real dataset is the Human Connectome Project 7 T retinotopy (HCP) data (See Noah C. Benson and Others, "The Human Connectome Project 7 Tesla retinotopy dataset: Description and population receptive field analysis," Journal of Vision, vol. 18, no. 13, pp. 1-22 Dec. 2018). Diffeomorphic retinotopic mapping was also achieved with HCP data. In addition, the Beltrami coefficients were obtained that quantify angle distortions for each subject. The method produces diffeomorphic results and minimizes the angle distortion, two important conditions for a valid retinotopic mapping research.

Problem Restatement

Figure 3:
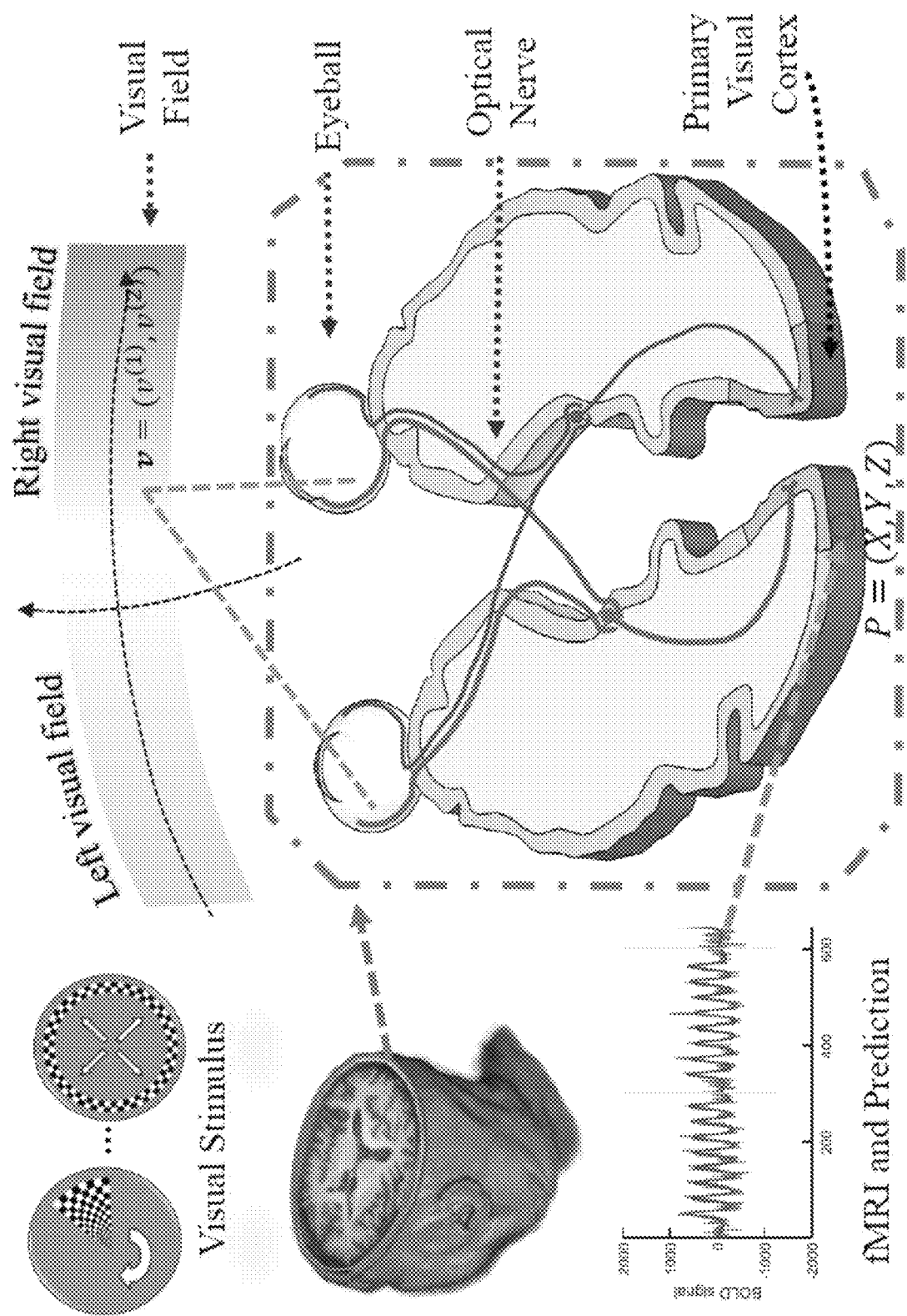
FIG. 3 illustrates a human visual system in accordance with various exemplary embodiments.

A problem involved here is restated in a biological intuitive and mathematically rigorous way. Assume there is a light spot on point v $(v^{(1)}, v^{(2)}) \in \mathbb{R}^2$ in the visual field, as shown in FIG. 3, an illustration of visual system to the visual cortex. After the visual system's perception, propagation, and dispensation, the light spot will eventually active a population of neurons. The main purpose of retinotopic mapping is to find the center v and the extent $\sigma \in \mathbb{R}^+$ of its receptive field on the retina, for each point $P=(X, Y, Z) \in \mathbb{R}^3$ on visual cortex.

fMRI provides a noninvasive way to determine v and $\sigma$ for P, based on the following procedure. (1) Design a stimulus time sequence s(t; v), such that the stimulus sequence is unique for every visual coordinate, i.e., s(t; $v_1$)≠s(t; $v_2$), $\forall v_1 \neq v_2$; (2) Present the stimulus sequence to an individual and record the fMRI signals from the visual cortex; (3) For each fMRI time sequence on a cortical location, y(t; P), determine the corresponding receptive field, including its center location v and its size $\sigma$ on the retina, that most-likely generated the fMRI signals. Specifically, given the neurons' spatial response r(v'; v, $\sigma$) (a predefined model depicts neural response around v) and the hemodynamic function h(t) (a model of the time course of neural activation to a stimulus), the predicted fMRI signal can be written as:

$$\hat{y}(v,\sigma)=\beta(\int r(v';v,\sigma)s(t,v')dv')*h(t) \quad (1)$$

where, $\beta$ is a coefficient that converts the units of response to the unit of fMRI activation. Then the parameters v and $\sigma$ are given by minimizing the prediction error, $$(v, \sigma) = \arg\min_{(v,\sigma)} |\hat{y}(v, \sigma) - y(P)|^2. \quad (2)$$

The retinotopic mapping of the entire visual cortex is obtained when (v, $\sigma$) is solved for every point on the cortical surface. It is known that nearby visual cortex will share nearby visual coordinates, i.e., topology preserving. The notion retinotopic mapping preserves topology means that, if $f$ is the retinotopic mapping, $f: P \mapsto v$, then a neighboring point P' of P, will have visual coordinate v' close to v. That is, $f$ is diffeomorphic in the domain of cortical surface.

Due to the low signal-noise ratio of fMRI, $f$ is not diffeomorphic. In an exemplary embodiment, a method is disclosed herein that achieves a diffeomorphic smoothing on $f$, such that the new mapping $\tilde{f}: P \mapsto \hat{v}$ is diffeomorphic and $\hat{v}$ is close to v. The Beltrami coefficient is adopted to quantify the diffeomorphism, $$\mu_f = \frac{(E - G + 2iF)}{\left(F + G + 2\sqrt{EG - F^2}\right)}, \quad (3)$$

where $$g(\hat{v}) = \begin{pmatrix} E(\hat{v}) & F(\hat{v}) \\ F(\hat{v}) & G(\hat{v}) \end{pmatrix}$$

is the metric tensor. If $|\mu|<1$ then $f$ is diffeomorphic. Furthermore, the bigger $\mu_f$ is, the larger angle deviation is. Therefore, the diffeomorphism defined in this way also provides a measure of angle deviation. The aim is to find $\hat{v} = \hat{f}(P)$, such that, $$\hat{v} = \arg \min_{\hat{v}} \int |v - \hat{v}|^2 ds, \text{ s.t. } |\mu_f| < 1 \quad (4)$$

Model and Method
Model in Discrete

Figure 4:
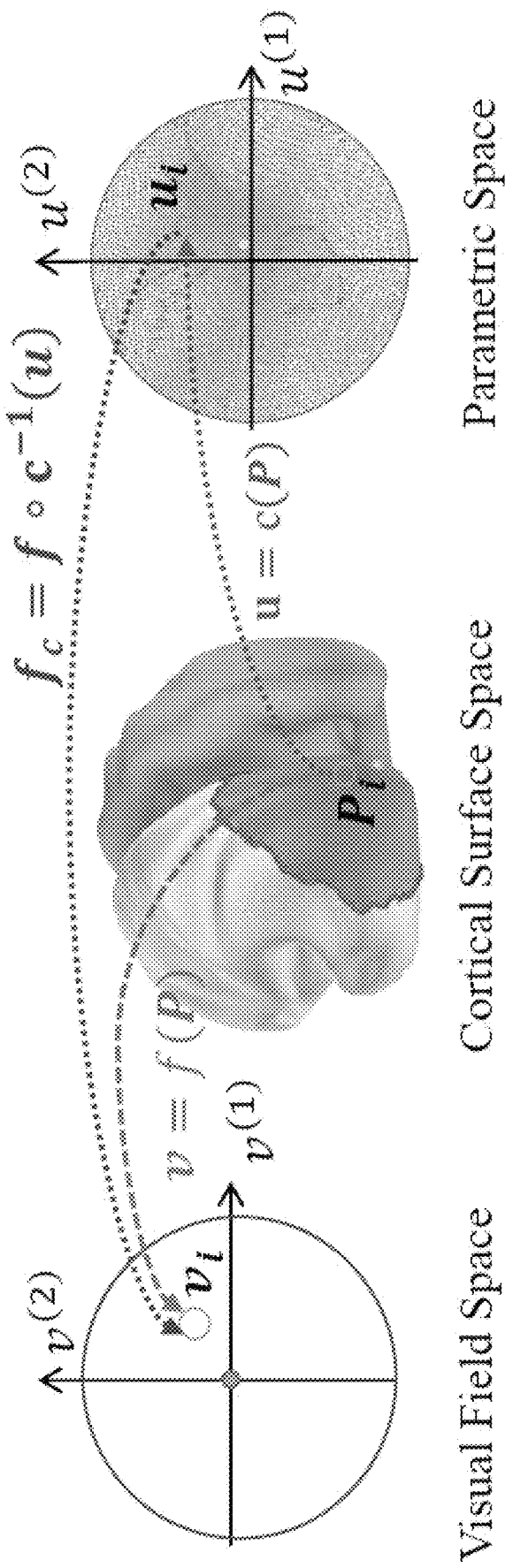
FIG. 4 illustrates several spaces and relations between them in accordance with various exemplary embodiments.
Figure 5:
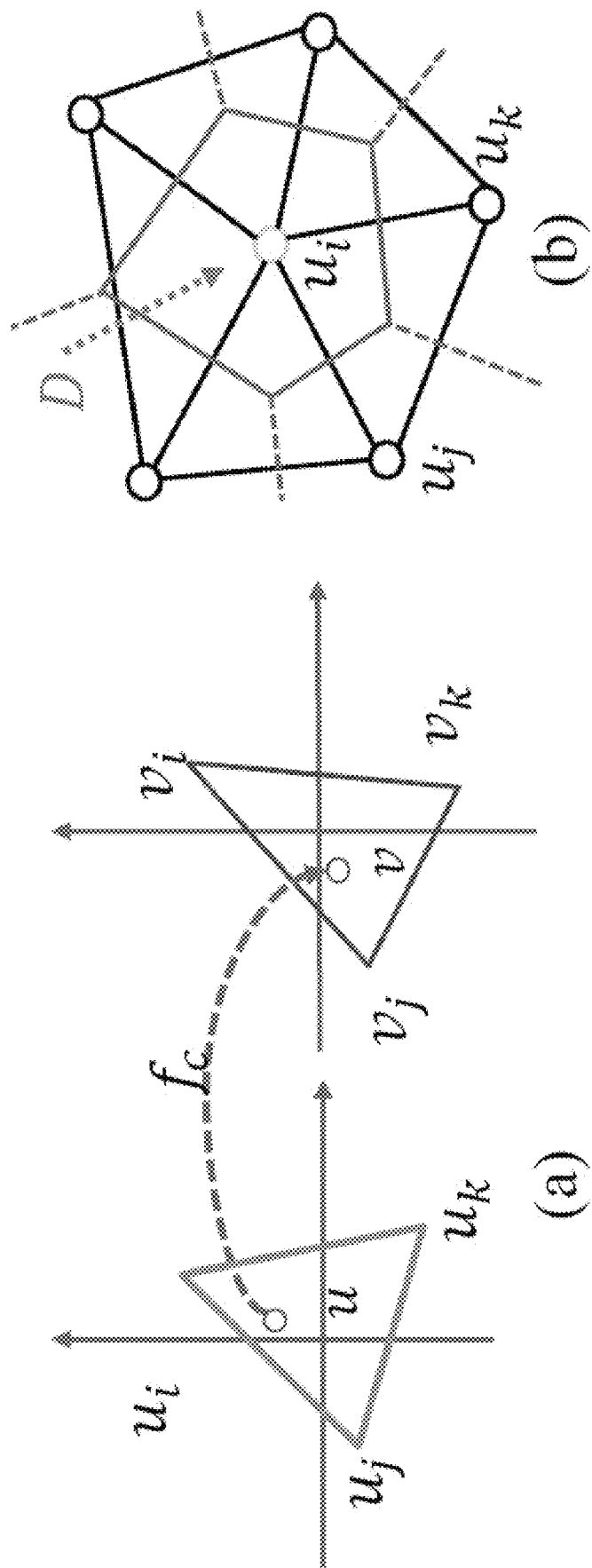
FIG. 5 illustrates (a) approximate a mapping in discrete and (b) a divergence approximation on the vertex ring in accordance with various exemplary embodiments.
Figure 6:
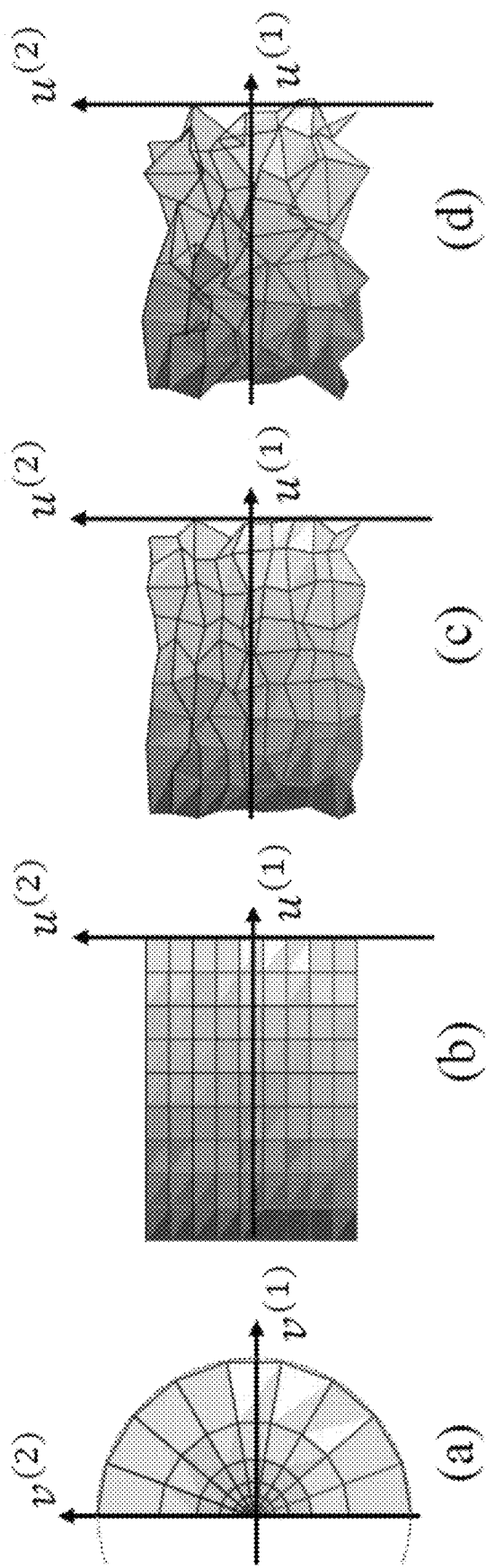
FIG. 6 illustrates a function domain, mapping result, and mapping results with noise in accordance with various exemplary embodiments: (a) mapping domain on the visual field; (b) mapping result without noise; (c) mapping result with weak noise (Peak Signal-Noise Ratio (PSNR)=20 dB); and (d) mapping result with strong noise (PSNR=10 dB)

In practice, cortical surface S is usually not an analytical function but consists of a bunch of vertices $V_S$ and triangular faces $F_S$, i.e. $S_S=(F_S, V_S)$. Similarly, visual space can also be discretized. Instead of taking another discretization, it is beneficial to take the same discretization as S. Then, the remaining problem is to find a visual coordinate $v_i$ for every vertex $P_i \in V_S$. In an exemplary embodiment, the problems are analyzed and solved on 2D instead of the original 3D cortical surface. Since diffeomorphism is transitive (If $f$ and c are both diffeomorphic function, then the composite function $f \cdot c$ is also diffeomorphic), a method in the present disclosure computes a conformal mapping (diffeomorphic and angle preserving) from the occipital region of the cortex to a parametric disk to simplify the problem to 2D. As shown in FIG. 4, an illustration of several spaces and relations between them, the gray colored region is mapped to the unit disk by c: $P \mapsto u$, $u=(u^{(1)}, u^{(2)}) \in \mathbb{R}^2$.

Although conformal mapping is angle preserving, it introduces distance distortion. To reduce the distortion, the method cuts a geodesic disk patch: picks a point on the cortical surface that corresponds to the fovea as the center point, then calculates the geodesic distances from all cortical position to the center point and only keep the portion of cortical surface whose geodesic distance to the center point is within a certain value. If $f_c = f \cdot c^{-1}$: $u \in \mathbb{R}^2 \mapsto v \in \mathbb{R}^2$ is solved with constraint $|\mu_{f_c}|<1$, then diffeomorphic retinotopic mapping is obtained by $f = f_c \cdot c$. Accordingly, Eq. (4) is simplified to, $$\hat{f}_c = \arg \min_{f_c} \int |f_c - \hat{f}_c|^2 du, \text{ s.t. } |u_f| < 1 \quad (5)$$

To solve Eq. (5) in discrete, the energy is formed as, $$E = \Sigma_i |F_i - \hat{F}_i|^2 + \lambda_1 |\mu_i|^2 + \lambda_2 |\nabla \hat{F}_i|^2 \quad (6)$$

where $F_i = f_c(u_i)$ is the raw result from Eq. (2), $\hat{F}_i$ is to be solved, $\mu_i = \mu_{f_c}(\mu_i)$ is the Beltrami coefficient at $\mu_i$, $\lambda_1$ and $\lambda_2$ are constants. Compared to Eq. (5), gradient of $\hat{F}$, $\nabla \hat{F}_i$, is introduced to increase smoothness, and $|\mu_i|^2$ is used to reduce non-diffeomorphism as well as angle distortion.

Numerical Method

It is difficult to minimize the energy in Eq. (6) directly, as it mixes the Beltrami coefficient and the mapping function together. A solution is to alternatively solve with respect to function and Beltrami coefficient in separate steps. Tools are utilized to convert the mapping function and Beltrami coefficient back and forth.

Beltrami Coefficient

Since there is a parametric coordinate u for the cortical surface S, the definition, Eq. (3), can be simplified to, $$\mu_f = \left(\frac{\partial f}{\partial u^{(1)}} + i \frac{\partial f}{\partial u^{(2)}}\right) / \left(\frac{\partial f}{\partial u^{(1)}} - i \frac{\partial f}{\partial u^{(2)}}\right). \quad (7)$$

Given the explicit form of function $f(u)$, $\mu_f$ is computed according to Eq. (7). In the discrete case, $f_c$ is interpreted linearly on each triangle. As shown in FIG. 5(a), for u within the triangle $\Delta u_i u_j u_k$, $f_c(u) = \alpha_i v_i + \alpha_j v_j + \alpha_k v_k$, where $v_1 = f_c(u_i)$, $v_j = f_c(u_j)$, and $v_k \to f_c(u_k)$. FIG. 5(b) illustrates the divergence approximation on the vertex ring. The coefficients $\alpha_i$, $\alpha_j$, and $\alpha_k$ are called barycentric coefficients. Specifically, $\alpha_i$ (similarly for $\alpha_j$ and $\alpha_k$) is the area portion of triangle $\Delta u u_j u_k$ to $\Delta u_i u_j u_k$, i.e. $\alpha_i = \text{Area}(\Delta u u_j u_k)/\text{Area}(\Delta u_i u_j u_k)$. Now the Beltrami coefficient $\mu_{f_c}$ is computed according to Eq. (7). It is easy to see that $\mu_{f_c}$ is a constant for each triangle.

Linear Beltrami Solver (LBS)

LBS is introduced to recovery function $f=(f^{(1)}, f^{(2)})$ for the given Beltrami coefficient $\mu = \rho + i\tau$. According to the definition in Eq. (7), the following is the result, $$\left(\frac{\partial f}{\partial u^{(1)}} + i \frac{\partial f}{\partial u^{(2)}}\right) / \left(\frac{\partial f}{\partial u^{(1)}} - i \frac{\partial f}{\partial u^{(2)}}\right) = \rho + i\tau. \quad (8)$$

After re-organizing Eq. (8) and eliminating $f^{(2)}$, the following is derived, $$\nabla \cdot A \nabla f^{(1)} = 0, \quad (9)$$

where $$A = \begin{pmatrix} \alpha_1 & \alpha_2 \\ \alpha_2 & \alpha_3 \end{pmatrix}, \alpha_1 = \frac{(\rho-1)^2 + \tau^2}{1 - \rho^2 - \tau^2}, \alpha_2 = \frac{-2\tau}{1 - \rho^2 - \tau^2}$$

and $$\alpha_3 = \frac{1 + 2\rho + \rho^2 + \tau^2}{1 - \rho^2 - \tau^2}, \nabla f^{(1)} = (\partial f^{(1)}/\partial u^{(1)} + \partial f^{(1)}/\partial u^{(2)}),$$

and the divergence $\nabla \cdot$ on vector $G = A\nabla f^{(1)} = (G^{(1)}, G^{(2)})$ is defined as $\nabla \cdot G = \partial G^{(1)}/\partial u^{(1)} + \partial G^{(2)}/\partial u^{(2)}$. By solving the partial equation Eq. (9) with certain boundary conditions, $f^{(1)}$ is solved. Similarly, $f^{(2)}$ is solved.

In the discrete case, the function is linearly interpreted on each triangle. The gradient of $f$, $\nabla f(u)$, can be written out. For the divergence on vector G, $\nabla \cdot G$, it is approximated on the dual cell of each vertex (a cell consisted of circumcenters of neighboring triangles). As shown in FIG. 5(b), consider the vertex $u_i$ with its neighbors $N(u_i)$, the divergence on vector G is approximated by, $$\nabla \cdot G = \frac{1}{|D|} \int_{\partial D} G ds = \frac{1}{|D|} \sum_{T_j \in N(u_i)} G_{T_j} \cdot (u_k - u_j) \quad (10)$$

FIG. 5(a) is an illustration of approximate the mapping in discrete. Applying the approximations, the result is a linear equation for each $f_i$ together with its neighboring vertices, according to Eq. (9). Finally, $f$ is solved efficiently by collecting all the equations and write them in a matrix form.

Laplacian Smoothing and Chopping

Now, the function and Beltrami coefficient are converted. The purpose is to make a smooth result. The next step is to apply the smooth operation on the function and Beltrami coefficient by the Laplacian smoothing. For instance, to get a smooth Beltrami coefficient v, the following is solved, $$v = \underset{v}{\operatorname{argmin}} \int |\nabla v|^2 + \lambda |v - \mu|^2 ds \quad (11)$$

where $\lambda$ is a constant. Eq. (11) can be efficiently solved by its Euler-Lagrange equation $(-\nabla \cdot \nabla + 2\lambda I)v = 2\lambda \mu$.

Although the non-diffeomorphism is penalized in Eq. (6), if there is a consistent point whose $|\mu| > 1$, it breaks the diffeomorphic result. To avoid this situation, one can shrink $v'$ $v/|v|$, if $|v| > 1$. This process is called Chop.

Algorithm

An overall smoothing process is summarized in the following Algorithm 2

---

Algorithm 2: Diffeomorphic Smoother

Input: Retinotopic coordinates $\{v_i\}$ of each vertex
Result: Smoothed retinotopic coordinates $\hat{v} = \{\hat{v}_i\}$
1  begin
2  |    $\hat{v}_i \leftarrow v_i$, for each vertex
3  |    repeat
4  |    |    Compute $\mu$ for $\hat{v}$, by Eq. (7);
5  |    |    Get v by Laplacian smoothing $\mu$, by Eq. (11);
6  |    |    Chop non-diffeomorphic according to
   |    |    v' = v/|v|;
7  |    |    Compute new mapping $\hat{v}$ by LBS on v';
8  |    until max $|\mu| < 1$;
9  |    return $\hat{v}$
10 end

---

Results

Synthetic Data

Performance of the algorithm may be evaluated on synthetic data. The ground truth mapping is given by, $$u^{(1)} + iu^{(2)} = \log(v^{(1)} + iv^{(2)}) \quad (12)$$

Figure 7:
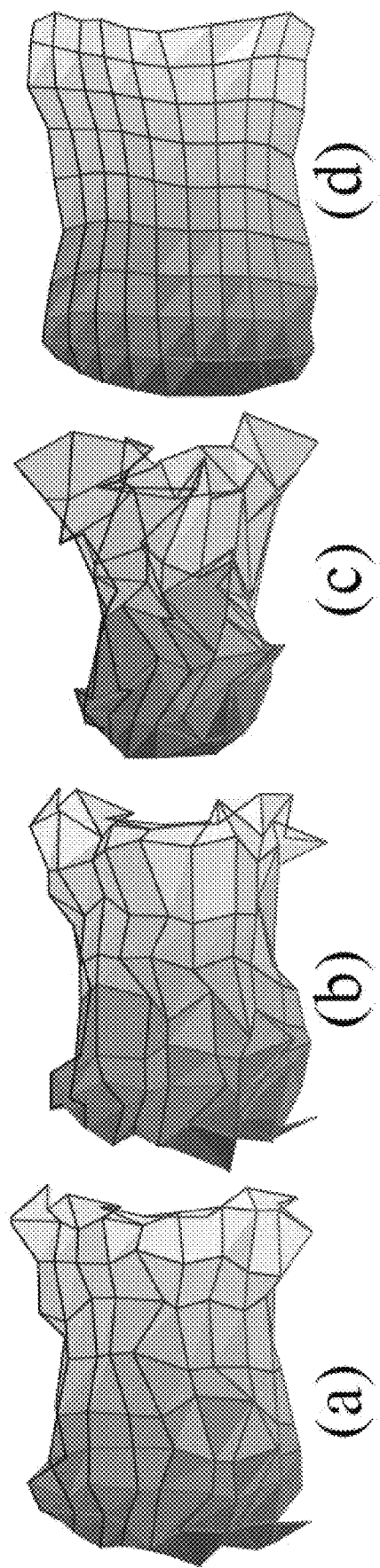
FIG. 7 illustrates smoothing results for map with big noise in accordance with various exemplary embodiments: (a) average smoothing; (b) median smoothing; (c) Laplacian smoothing; and (d) exemplary smoothing.

Then log function is chosen as it is a good approximation of the retinotopic mapping from visual space to the flattened cortical surface. As shown in FIG. 6(a), the visual domain is mapped to the parametric space FIG. 6(b). Also, the results show the mapping with a small amount of noise in FIG. 6(c) and a large amount of noise in FIG. 6(d). Several smoothing methods are applied on the synthetic mapping data in both small and big noise cases, including Average Smoothing in FIG. 7(a), Median Smoothing in FIG. 7(b), and Laplacian Smoothing in FIG. 7(c) and their results were compared with the method in the present disclosure in FIG. 7(d). The results for the big noisy case are shown in FIG. 7. All of them are spatial smoothing procedures. As shown in FIG. 7(a), Average Smoothing takes the average around each neighborhood. As shown in FIG. 7(b), Median Smoothing takes the median value of each neighborhood. As shown in FIG. 7(c), Laplacian smoothing is the so-called "Perfect Smoothing". Except for the method of the present disclosure as shown in FIG. 7(d), all other smoothing procedures process the coordinates $u^{(1)}$ and $u^{(2)}$ separately. The following Table 1 lists the performance metric of all the methods.

TABLE 1

Comparing different smoothing methods by four metrics, mean value deviation of function, the max of the function deviation, and the number of overlapped triangles (non-diffeomorphic triangles).

| Method | Value Deviation | | # Flipped Triangles |
|---|---|---|---|
|  | Mean | Max |  |
| Before Smoothing | 0.25/0.40 | 0.64/1.05 | 19/56 |
| Average Smoothing | 0.18/0.24 | 0.62/0.77 | 3/8 |
| Median Smoothing | 0.22/0.28 | 0.69/0.83 | 2/24 |
| Laplacian Smoothing | 0.23/0.36 | 0.66/0.92 | 11/43 |
| The Present Smoother | 0.19/0.22 | 0.65/0.75 | 0/0 |

Value deviation means error to the ground truth. For cells with two values like "A/B", "A" is the result for the map with a small added noise (PSNR = 20 dB); while "B" is the result for the map with a big added noise (PSNR = 10 dB).

It was found that (1) all the smoothing methods helped reduce the noise, and reduce flipped triangles (i.e. triangle violates the topology preserving condition); (2) with a small amount of added noise, the topology violation problem is not severe, average smoothing can also achieve almost diffeomorphic results; (3) however, with a large amount of added noise, only exemplary methods in the present disclosure can achieve a diffeomorphic result.

HCP Data

With 7-Tesla MRI systems, the signal-to-noise ratio of retinotopic mapping has been dramatically improved. Still, the mapping is noisy and non-diffeomorphic. A smoother in the present disclosure may be applied to data from a 7 T MRI system. The details of the dataset are known (See Noah C. Benson and Others, "The Human Connectome Project 7 Tesla retinotopy dataset: Description and population receptive field analysis," Journal of Vision, vol. 18, no. 13, pp. 1-22 Dec. 2018). Because smoothing is a primary interest here, the evaluation process used publicly available data of the decoded retinotopic coordinate for each cortical vertex of five subjects, and evaluated the performance of an exemplary smoother. The total number of flipped triangles for raw data is 1313, for the average, median, and Laplacian methods are 1289, 1312, and 1337, respectively. The smoother has no flipped triangles (i.e., zero).

Figure 8:
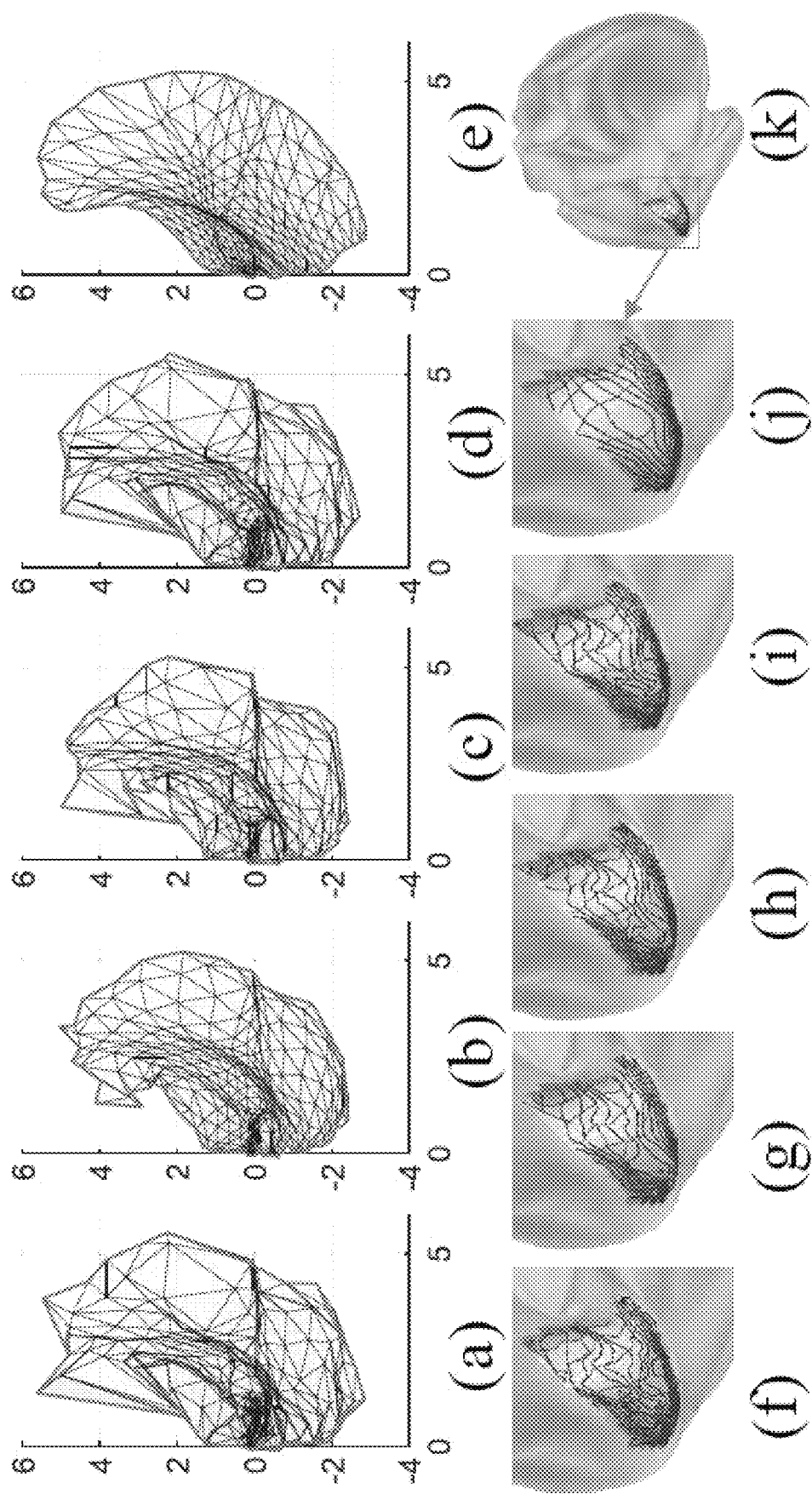
FIG. 8 illustrates a subject's left retinotopic mapping in accordance with various exemplary embodiments: (a) raw retinotopic mapping; (b)-(e) smoothing results of average, median, Laplacian, and proposed smoothing methods; (f) the raw mapping on cortical surface; (g)-(j) smoothing results on inflated surface of each method, in the same order of (b)-(e); and (k) the left inflated cortex.

For a persuasive and intuitive comparison, FIG. 8 shows the retinotopic mapping of the left hemisphere of the subject, and the smoothed results of different methods. As shown in FIGS. 8(a) and (f), the original mapping is not diffeomorphic. FIGS. 8(b)-(e) show smoothing results of average, median, Laplacian, and smoother methods respectively while FIGS. 8 (g)-(j) show smoothing results on inflated surface of each of the methods in FIGS. 8(b)-(e) respectively. FIG. 8(k) is an illustration of the left inflated cortex. Although all smoothing methods improved the smoothness, only an exemplary smoother herein can generate diffeomorphic result, especially near the fovea.

Conclusion

The smoother of the present disclosure adopts the Beltrami coefficient to quantify diffeomorphism of retinotopic mapping and forms a mathematical model to generate diffeomorphic maps. The smoother produces results of diffeomorphism and minimizes angle distortion.

Methods and Systems for Processing Functional Imaging Data

In an exemplary embodiment, a method is disclosed that applies a topological receptive field model (tRF) for human retinotopic mapping, as shown in FIGS. 9-12.

Summary

The mapping between visual inputs on the retina and neuronal activations in the visual cortex, i.e., retinotopic map, is an essential topic in vision science and neuroscience. Human retinotopic maps can be revealed by analyzing the functional magnetic resonance imaging (fMRI) signal responses to designed visual stimuli in vivo. Neurophysiology studies indicated that visual areas are topological (i.e., nearby neurons have receptive fields at nearby locations in the image). However, conventional fMRI-based analyses generate nontopological results because they process fMRI signals on a voxel-wise basis, without considering the neighbor relations on the surface. The present disclosure applies a topological receptive field (tRF) model which imposes the topological condition when decoding retinotopic fMRI signals. More specifically, the method parametrizes the cortical surface to a unit disk, characterizes the topological condition by tRF, and employs an efficient scheme to solve the tRF model. The framework was tested on both synthetic and human fMRI data. Experimental results showed that the tRF model removes the topological violations, improves model explaining power, and generates biologically plausible retinotopic maps. This framework is general and can be applied to other sensory maps.

Introduction

It is of great interest to quantify, simulate, and understand the relation between the visual inputs and the neuronal response with the retinotopic maps. A precise retinotopic map provides opportunities to understand or even simulate various aspects of the visual system. For instance, the complex-log model, which depicted a rough position map between the retina and the primal visual cortex (V1), explained the dynamics of spiral visual illusions. The retinotopic maps discovered some stable visual regions. Additionally, retinotopic map research holds great promise in understanding brain plasticity and improving rehabilitation's efficacy from visual impairments. Further, retinotopic maps have been clinically adopted to monitor the progress and recovery under amblyopia treatment, a disorder that affects about 2% of children and may cause significant visual impairment if untreated.

Typically, human retinotopic maps are obtained in vivo by analyzing cortical functional magnetic resonance imaging (fMRI) response signals to visual stimuli. Since the first fMRI work on retinotopic mapping, several analysis models were proposed to decode perception parameters from the noisy fMRI signals. Among them, the population receptive field (pRF) model generates state-of-the-art results and becomes a cornerstone in fMRI signal analysis of retinotopic maps.

Although the pRF model achieved great success, the pRF results are not topological. The topological condition is an essential requirement of retinotopic maps since neurophysiology studies have revealed nearby neurons have receptive fields at nearby locations in the image (the topological condition). The topological condition is also the requirement of the vision system's hierarchical organization: each visual area represents a unique map of a portion of retina. If there are duplicated representations in a visual area, this visual area should be further divided into more areas. Besides, it is challenging to infer accurate visual-related quantification without a topological retinotopic map, e.g., visual boundaries, cortical magnification factor, visual anisomery. Therefore, topological retinotopic map results are vital for neuroscience research.

A variety of methods have been developed to reduce topological violations in the postprocessing of pRF results. For instance, the model fitting is widely used to fit the decoded parameters with an algebraic model for V1-V3. Smoothing methods, e.g., Laplacian smoothing, process visual parameters one by one but cannot ensure the topological condition. Surface registration of retinotopic mesh is also developed for post-processing of pRF results. However, none of the existing methods have considered the topological condition when decoding fMRI signals. It is advantageous but challenging to impose the topological condition when decoding fMRI. First, the topological condition is different across visual areas, while the precise visual areas are delineated upon the decoding results. One may think the segmentation is available through the anatomical surface. However, all anatomical-based segmentation is not accurate, limited by its modality. Second, because the fMRI signal is noisy, it is challenging to segment visual areas from the noisy decoded results.

Various exemplary embodiments apply a topological receptive field (tRF) framework, which imposes the topological conditions by integrating the topology-preserving segmentation and topological fMRI decoding into a coherent system. The framework first segments the visual areas by preserving the prior connectivity pattern of visual areas based on initial decoding and then models the fMRI decoding with the topological condition within each visual area. Since the new fMRI decoding results can refine the segmentation, the framework repeats the segmentation and decoding until theoretically guaranteed convergence.

This exemplary framework has been validated on both synthetic data and human retinotopy data. The experiments showed the superiority of tRF over other methods, including the population receptive field (pRF) model, post-processing by model fitting, smoothing, or registration methods. In summary, (1) it is the first method that enforces the topological condition in decoding retinotopic fMRI signals; (2) it is also the first automatic visual area segmentation with the topology organization preserved. The framework is general and can be extended to other sensory maps because most of the human perception maps are spatially organized, e.g., auditory map is spatially related to sound frequency.

Retinotopic Mapping Experiment

Figure 9:
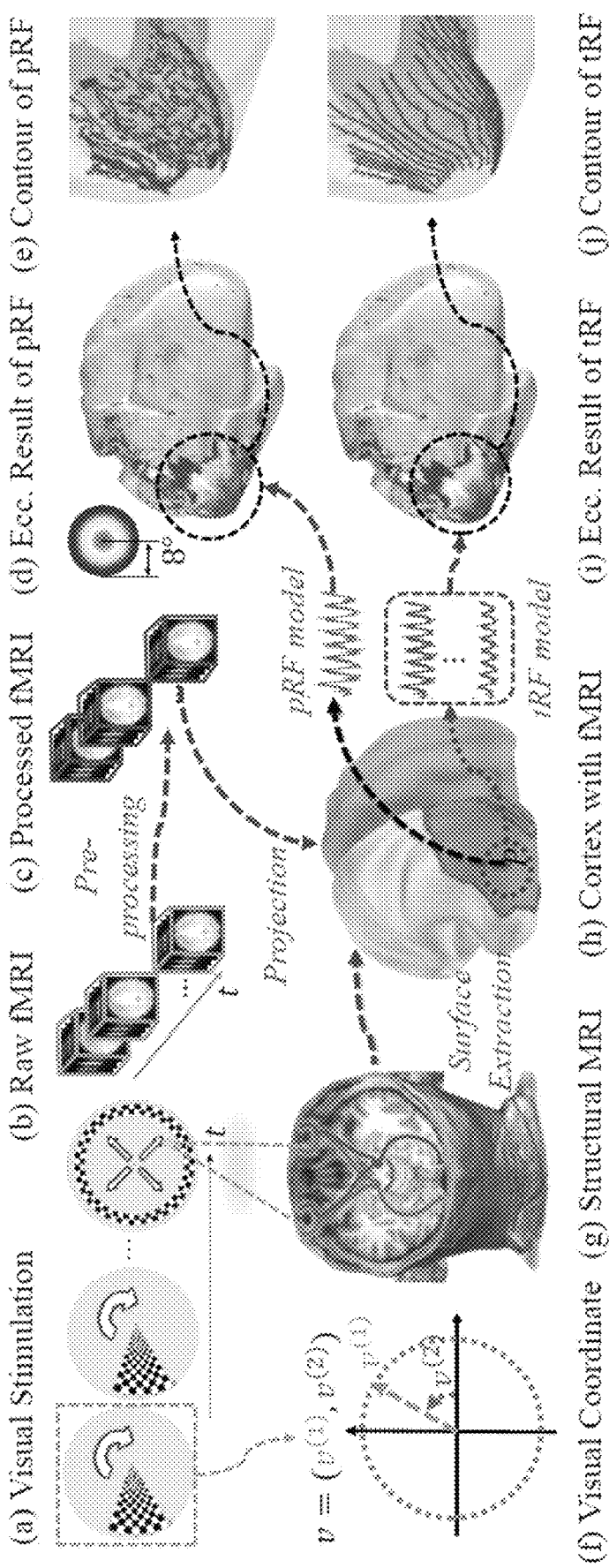
FIG. 9 illustrates a retinotopic map experiment and the pipelines of population receptive field (pRF)/topological receptive field (tRF) models in accordance with various exemplary embodiments.
Figure 10:
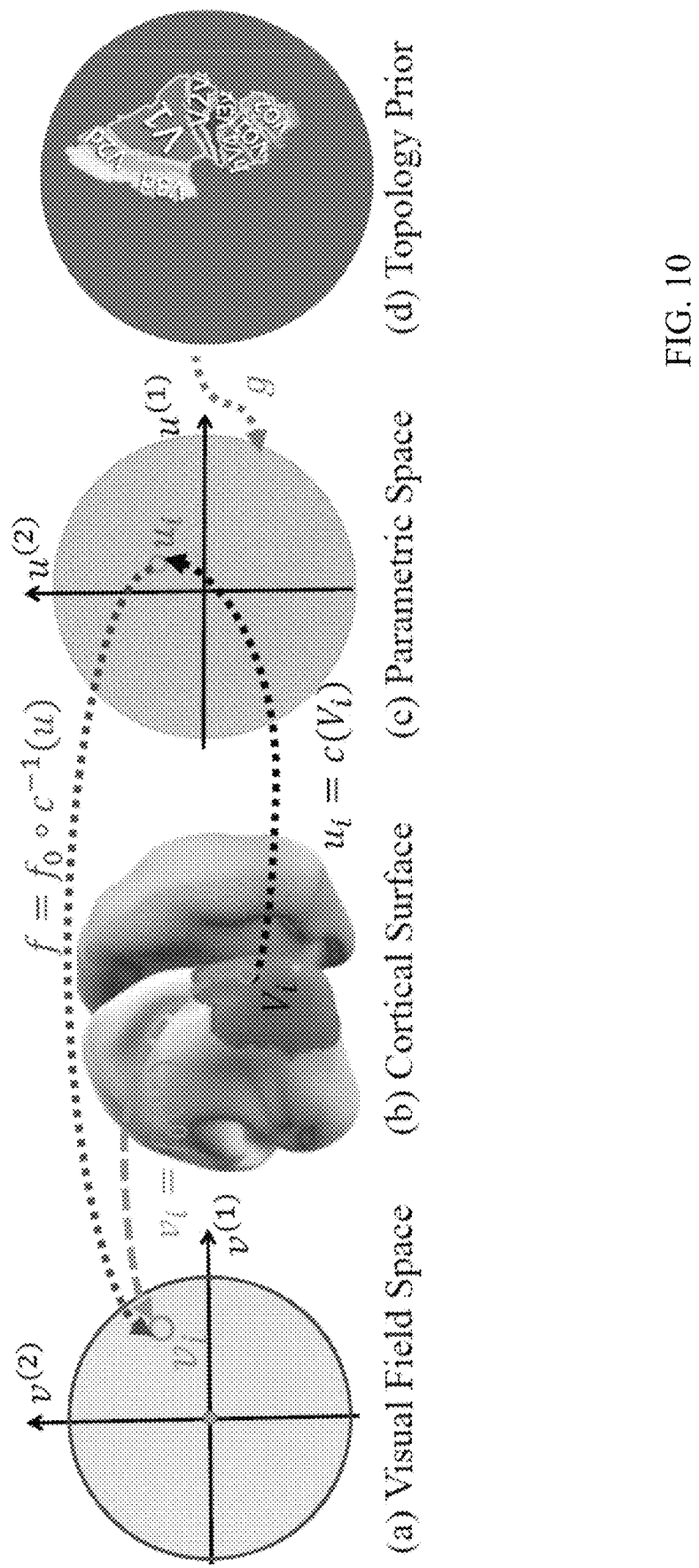
FIG. 10 illustrates a parametrization and segmentation process in accordance with various exemplary embodiments: (a) the visual field; (b) the region of interest (ROI); (c) conformal parametrization of ROI; and (d) the topology-prior (the label is defined for each point)
Figure 11:
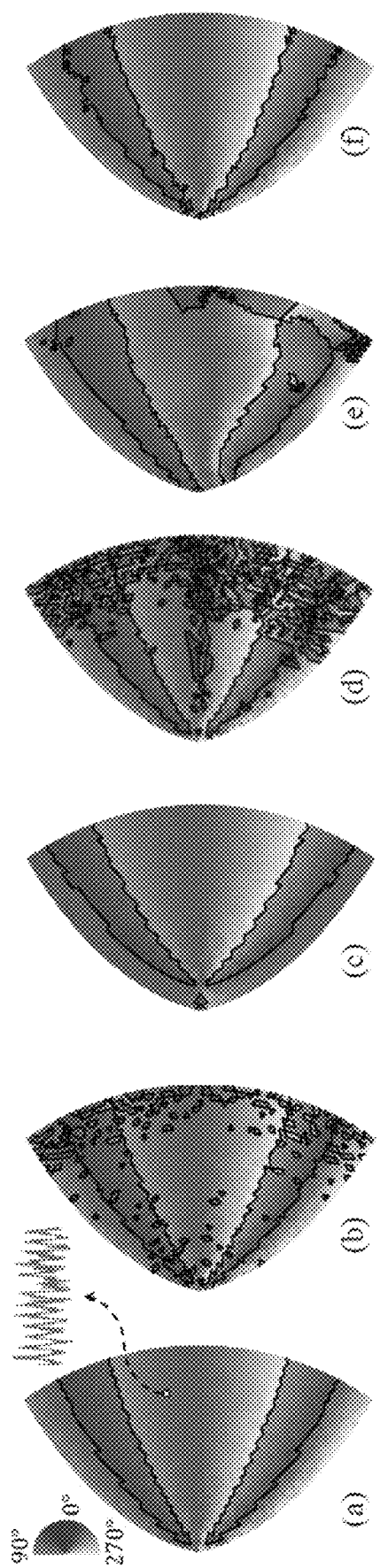
FIG. 11 illustrates comparison of various methods for the V1-V3 model in accordance with various exemplary embodiments: (a) Ground-truth; (b) pRF; (c) model-fitting; (d) smoothing; (e) registration; and (f) the proposed tRF.
Figure 12:
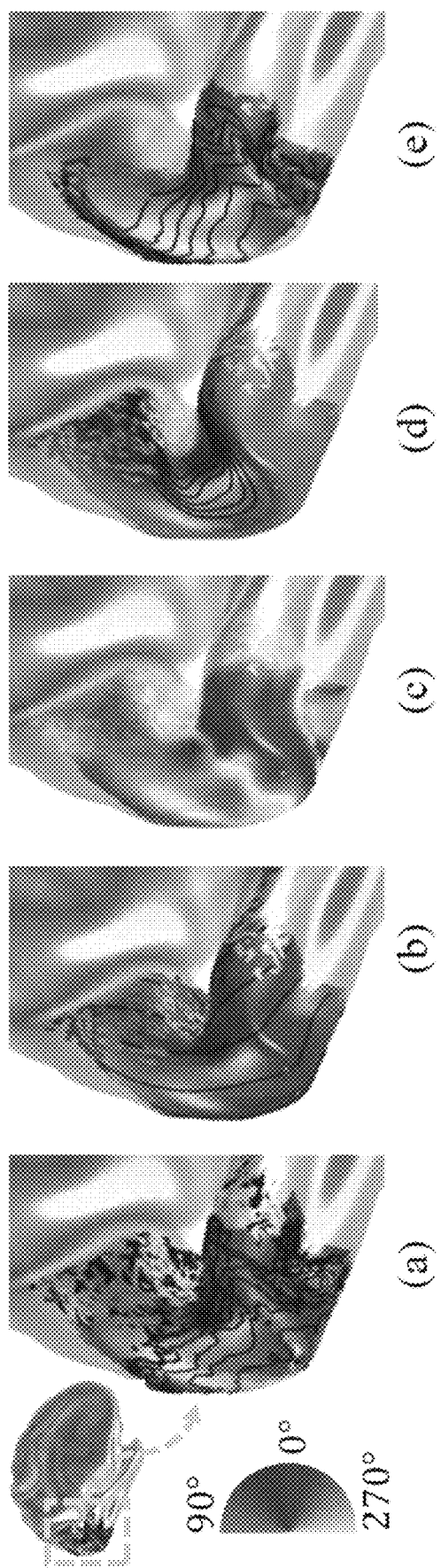
FIG. 12 illustrates results of: (a) pRF; (b) model-fitting; (c) smoothing; (d) registration; and (e) tRF in accordance with various exemplary embodiments.

Here is a brief introduction of an exemplary retinotopic mapping experiment. Such an experiment acquires both structural MRI and fMRI signals, as illustrated in FIG. 9. The structural MRI (FIG. 9g) is used to reconstruct the cortical surface. The fMRI (FIG. 9b) is acquired to monitor neuron activities during the visual stimuli (FIG. 9a). The visual stimulation is carefully designed to encode the visual space (FIG. 9f) uniquely. Before the analysis, the fMRI volumes are preprocessed (FIG. 9c) and projected onto the cortical surface (FIG. 9h). Eventually, for each subject, there is a high-quality anatomical/structural cortical surface in the form of discrete manifold S=(V, E, F) (where V is the surface vertex set, E is the edge set, and F is the face set), together with fMRI time series $y_i(t)$ for each vertex $V_i \in V$ on the cortical surface.

pRF Model

The population receptive field (pRF) model decodes fMRI signals vertex by vertex. Namely, on the measurement $y_i(t)$, the pRF predicts perception parameters, including the population perception center $v_i=(v_i^{(1)}, v_i^{(2)})$ and population receptive field size $\sigma_i$. The model takes the polar coordinates for the visual fields, as shown in FIG. 9f. Namely, $v^{(1)}$ and $v^{(2)}$ are the eccentricity and polar angle, respectively. Given the receptive model $r(v'; v_i, \sigma)$, and the hemodynamic model $h(t)$, the predicted fMRI is, $\hat{y}(t; v_i, \sigma)=\beta(\int r(v'; v_i, \sigma)s(t, v')dv')*h(t)$, where $\beta$ is the activation level (a time-independent scalar). The perception center $v_i$ and population receptive field size $\sigma_i$ are estimated by minimizing the error between the measured and predicted fMRI activation signal, $$(v_i, \sigma_i) = \arg\min_{(v_i,\sigma_i)} E_p = \int (\hat{y}(t; v_i, \sigma_i) - y_i(t))^2 dt. \quad (13)$$

Solving Eq. 13 for all points generates the pRF retinotopic map. This model shows a typical pRF retinotopic map on the visual cortex in FIG. 9d. Still, a large portion of the result is not topological (the visual coordinates' contour curves are messed up in FIG. 9e). An exemplary framework applies the tRF (FIGS. 9i & j) to improve the retinotopic maps.

Parametrization

First, a parametrization is established between the 3D visual cortex and the 2D planar disk. A geodesic patch containing the visual areas is cut. In specific, the framework picks a point $p_0$ on the cortex, then encloses a patch P comprising cortical points within a certain geodesic to $P_0$, as illustrated in FIG. 10b. The next step is to compute the conformal parametrization for patch P to planar disk D. If $c: P\rightarrow D$ is the conformal parameterization, then $u_i=c(V_i)$ where $u_i\in \mathbb{R}^2$ is the parametric coordinate for $V_i$. The conformal mapping may be done via spherical conformal mapping of the double coverings of surface patches, followed by stereographic projection. With the parametrization c, the topology condition within the planar domains can be discussed. FIGS. 10(a), (c) and (d) illustrates the visual field, the conformal parametrization of the region of interest, and the topology-prior respectively.

Topology Conditions

The topology conditions have two inferences. First, the visual coordinates are topological with respect to the surface parametrization within each visual area (this condition is called the topological condition within each visual area). Second, because the human visual cortex is organized into several visual areas, and the visual areas hold the same organization (for instance, V1 is adjacent to V2d and V2v) across subjects (to distinguish, this condition is called topology-preserving condition across visual areas).

Both conditions can be quantified by the Beltrami coefficient of quasiconformal maps. Namely, the framework disclosed herein uses the Beltrami coefficient to enforce a topology-preserving surface segmentation and uses the concept again to ensure the topological condition for the retinotopic map within each visual area. The following will introduce the Beltrami coefficient's definition and then explain how it is adopted into these two conditions.

An orientation-preserving homeomorphism $\varphi(z): \mathbb{C} \rightarrow \mathbb{C}$ is quasiconformal if it satisfies the Beltrami equation $$\frac{\partial \varphi(z)}{\partial \bar{z}} = \mu_\varphi \frac{\partial \varphi(z)}{\partial z}$$

where $\mu_\varphi$ is the Beltrami coefficient satisfying $|\mu_\varphi|_\infty<1$. In particular, if $\mu_\varphi=0$ then $\varphi$ is conformal.

The topological condition requires the retinotopic map from each visual area to the retina to be orientation consistent. The orientation (biologically the visual field sign, VFS) for the visual area can be either positive or negative, depending on the parametrization and visual area. Once fixing a parametrization, the map (from parametric space to retina) orientation for a specific visual area is then fixed. Of course, one can treat the negative visual field area to be positive by flipping the parametrization vertically ($u'^{(2)})=-u^{(2)}$). Without losing generality, considering a positive visual area, it is required that the VFS is consistently positive. Mathematically, it requires the Beltrami coefficient $\mu_f$, associated with the retinotopic map from parametric space (within the unit disk) to visual field space $f: u_i \mapsto +v_i$, satisfies $|\mu_f|<1$.

A registration-akin method may be used for topology-preserving segmentation. The method diffeomorphically morphs the topology-prior (which has the right topology) to the subject's parametrization disk and then uses prior's label information for the subject. The segmentation is topology-preserving if the morphing is diffeomorphic. Let $g: D\rightarrow D$ be the morph function. If the Beltrami coefficient $\mu_g$ satisfies $|\mu_g|_\infty<1$, g is diffeomorphic. Compared to retinotopic registration, where visual coordinates are required when defining a template, the prior label is required in this exemplary framework, which is easier to give and reduces the model visual coordinates hypothesis.

tRF Model

Here is an introduction of the tRF model, which includes fMRI decoding $T=\{(v_i, \sigma_i)|V_i \in V\}$ and visual areas segmentation $L=\{L_i \in \mathbb{N} | V_i \in V\}$, (one value for an area) altogether.

Topology-Preserving Segmentation

A wrapping function g is searched that maximizes the label alignment between subject and wrapped-prior. However, there are no labels before segmentation. As an alternative, this framework maximizes the alignment between VFS of topology prior and VFS of a subject. Let $J=(F_J, E_J, u_J, L_J)$ be the topology-prior mesh, where $F_J$ is face set, $E_J$ is edge set, $u_J=\{u_j\}$ is vertex set and $L_J=\{L_j \in \mathbb{N} | u_j \in u_J\}$ is label set, $\hat{S}_g: D \rightarrow \{-1,1\}$ be the VFS for topology-prior after wrapping, and $s:=\text{sign}(1-|\mu_f|)$ be the VFS function of the subject, where $$\mu_f = \frac{\partial v}{\partial \bar{u}} / \frac{\partial v}{\partial u} (v = v^{(1)} + iv^{(2)} \text{ and } u = u^{(1)} + iu^{(2)}).$$

This framework models the registration by $E=\int_D |\hat{S}_g-s| + \lambda_g \int |\nabla g|^2 \, du$, such that $|\mu_g|<1$, where $|\hat{S}_g-s|$ is the VFS mismatch cost, and $\lambda_g$ is a positive constant that controls the smoothness of g. The mismatch cost is formulated to encourage the subject, and the wrapped topology-prior shares the same VFS at each position.

Topological fMRI Decoding

Without losing generality, for a positive orientated visual area $V^+$, the topological fMRI decoding model is to solve within the $V^+$ area, by $T=\arg\min \Sigma_{v_j \in V^+} \int |\hat{y}(t; v_j, \sigma_j)-y_j(t)|^2 dt + \lambda_v |\nabla v|_1^2 \, du$, s. t. $|\mu_f|<1$, where $|\nabla v|^2 = |\nabla v^{(1)}|^2 + |\nabla v^{(2)}|^2$. Similarly, the tRF model can be applied to the negative area by flipping the parametrization vertically. To avoid over smoothing, the values of $\lambda_v$ are chosen based on the Generalized Cross-Validation.

tRF Model

The tRF finds the visual parameters for the visual cortex via two modules, $$\hat{L} = L_J(g), \text{ where } g = \arg^{min}_g \int_D |\hat{S}_g - s| + \lambda_g \int_D |\nabla g|^2 du, \text{ s.t. } |\mu_g| < 1 \quad (14)$$

$$\hat{T} = \arg^{min}_{\hat{T}} \sum ui \in D \int (\hat{y} - y_i)^2 dt + \lambda_v |\nabla v|_1^2, \text{ s.t. } s(u_i) = \hat{s}(u_i|\hat{L}). \quad (15)$$

Numerical Method

A direct search for $(\hat{L}, \hat{T})$ is computationally infeasible because the number of parameters are typically high and $\hat{y}$ is also computationally heavy. The problem may be divided into two subproblems, segmentation and fMRI decoding, and the two subproblems are updated iteratively. Since both subproblems constrain the norm of Beltrami, a technique is introduced in advance, which is called topology-projection.

Topology-Projection with Smoothing

Given a map $f$, the topology-projection computes a smooth and topological map $f'$ with small changes of $f$ According to Measurable Riemannian Mapping Theorem, the Beltrami coefficient uniquely encodes a map upon suitable normalization. Therefore, a map can be manipulated by its Beltrami coefficient. If a map whose $|\mu_f| > 1$ for some points, its norm is adjusted for those points by $\mu'_f = a\mu_f/|\mu_f|$ (a=0.95 in this disclosure). Then $\mu'$ is used to recover the topological map $f'$. In specific, one can find $f'$ by solving $\nabla \cdot A \nabla f' = 0$, with Dirichlet boundary condition. Here A is a 2-by-2 matrix upon $\mu'_f$ [28], $\nabla$ and $\nabla$ are the gradient and divergence operators, respectively. $f'$ can be solved efficiently by writing $\nabla A \nabla$ as a matrix. After the topology-projection, Laplacian smoothing is applied to $f'$ to make it smooth.

Topology-Preserving Segmentation

To solve Eq. 14, it is divided into two subproblems: naïve g searching and topology projection. Specifically, (1) for $u \in u_f$, the target of g(u) is updated to nearest point g' such that $s(u_i) = s(g')$, since it minimizes the VFS mismatch; (2) the topological projection is used to fix the topological condition for g' (see SI for segmentation results).

Topological fMRI Decoding

Eq. 15 is also split into two subproblems: parameter searching and topology-projection. Specifically, (1) the topology-projection is used for each visual area respectively to get topological visual parameters T'; (2) the gradient descent is used to update T' parameters, $$T' \leftarrow T' - \eta \left\{ \left( \frac{\partial E_p}{\partial v(1)}, \frac{\partial E_p}{\partial v(2)}, \frac{\partial E_p}{\partial \sigma} \right) \right\}$$

where $\eta$ is a constant (updating step). The updated result T' is further used to improve the segmentation, described in Eq. 14.

Algorithm

The overall procedures of the tRF framework is summarized in the following Algorithm 3. Note that the updating step is decayed by $\eta^{(t+1)} = k_\beta \eta^{(t)}$, $k_\beta < 1$, to ensure tRF converges. Its convergence proof is provided in SM.

| Algorithm 3: The tRF framework |
|---|
| Input: Discrete region of interest S = (V, E, F); fMRI signal $y_i$ for each point; a tolerance $\epsilon \in R^+$; and a decay factor $k_\beta < 1$. |
| Results: The topology-preserving segmentation L and topological retinotopic map T = {($v_i$, $\sigma_i$)} that sufficiently explains the fMRI signal. |
| Solve the pointwise pRF parameter ($v_i$, $\sigma_i$) by Eq. 13 |
| Compute the conformal disk parametrization $u_i = c(V_i)$, $V_i \in V$ |
| Initialize T = {($v_i$, $\sigma_i$)}, and $\delta \leftarrow \infty$ |
| while $\delta > \epsilon$ do |
|     Compute the segmentation L, by solving Eq. 14 |
|     Update T' on given segmentation L by solving Eq. 15 |
|     $\delta = \max(T' - T)$, $T \leftarrow T'$, and $\eta^{(t+1)} \leftarrow k_\beta \eta^{(t)}$ |
| end |

Dataset

Synthetic Data

An exemplary framework has been evaluated on synthetic data. The evaluation process used double-sech model as ground truth and assigned a receptive field size $\sigma = k_2 v^{(1)}$ ($k_2 = 0.01, 0.02, 0.03$ for V1, V2, and V3, respectively). The next step is to generate the normalized fMRI signal $y_0(t)$ with a known specific stimulation pattern (see Kay, N., Benson, C., Jamison, K., Arcaro, M., Vu, A., Coalson, T., Essen, D. Van, Yacoub, E., Ugurbil, K., Winawer, J., Kay, K.: The HCP 7 T Retinotopy Dataset, https://osf.io/bw9ec/.) and add two levels of noise to the fMRI signal $y(t) = y_0(t) + r(t)$, where $r \sim N(0, \gamma)$ ($\gamma = 0.1$ and $\gamma = 0.5$ respectively).

Real Data with 7 T MRI System

An exemplary framework was also tested on the Human Connectome Project (HCP) dataset (See Benson, N. C., Jamison, K. W., Arcaro, M. J., Vu, A. T., Glasser, M. F., Coalson, T. S., Van Essen, D. C., Yacoub, E., Ugurbil, K., Winawer, J., Kay, K.: The Human Connectome Project 7 Tesla retinotopy dataset: Description and population receptive field analysis. J. Vis. 18, 1-22 (2018). https://doi.org/10.1167/18.13.23). The HCP dataset is a publicly available retinotopy dataset on 7 T fMRI scanners with high spatial and temporal resolutions.

Results

Results on Synthetic Data

The performance of an exemplary framework disclosed herein was compared with several methods, including the pRF model, the model fitting result, the Laplacian smoothing, and the registration method (which registers pRF to another parameterized Double-Sech template and uses the template's value). More specifically, given the noisy functional signal y(t) for each vertex, the errors were compared between methods' output and ground truth in Table 2, including the perception center error $|\Delta v|$, receptive field size error $|\Delta \sigma|$, and the numbers of triangles that violates the required VFS within its segmentation.

The results indicate that: (1) only the exemplary framework disclosed herein makes topological results ($T_n = 0$), and the smoothing achieved the worst results, which means the smoothing does not contribute to the exemplary method's topological results in topology-projection; (2) on the other hand, the smoothing method also achieved decent precision ($|\Delta v| \sim 2$); (3) the model-fitting method is promising in topological condition ($T_n < 5$). However, it is only applicable to the V1-V3 complex but not to other visual areas (see Table 3; the flipping number is significant due to regions beyond V3); (4) the TPS registration method can ensure the topology in theory. However, because of the noisy measure of retinotopic coordinates, the anchors/landmarks are noisy and may destroy the topological condition. Those results suggest the framework of the present disclosure achieves the best accuracy under topological condition. An illustrative comparison is provided in FIG. 11 for various methods. FIGS. 11(a)-(f) illustrate the results for the V1-V3 model by ground-truth method in FIG. 11(a), pRF model in FIG. 11(b), model-fitting method in FIG. 11(c), smoothing method in FIG. 11(d), registration method in FIG. 11(e), and the tRF framework in FIG. 11(f).

TABLE 2

A performance comparison (the smaller, the better) on synthetic data.

| Method | $|\Delta v|$ | $|\Delta \sigma|$ | $T_n$ |
|---|---|---|---|
| pRF Method | 2.924/2.313 | 0.902/1.100 | 393/483 |
| Smoothing | 2.827/2.288 | 0.863/1.021 | 469/528 |
| Registration | 3.549/3.518 | 0.974/0.971 | 440/444 |
| Model-fitting | 3.559/3.590 | 0.902/1.100 | 3/5 |
| tRF | 2.485/1.801 | 0.768/0.857 | 0/0 |

Results for $\gamma = 0.1$ (small noise) and $\gamma = 0.5$ (big noise) are separated by the "/" symbol.

Results on the Real Data

An exemplary tRF was applied to subjects in the HCP dataset. Since no ground-truth is available for the real dataset, the methods were compared based on the fMRI fitting goodness (the RMSE of fitting error $\bar{e}$) and the number of non-topology triangles ($T_n$) The fitting error $\bar{e}$ and topology violations $T_n$ for the first three observers were listed in Table 3. The tRF achieved the best fMRI fitting and zero topology violations. The results also showed the intuitive comparison between the methods for the first observer in FIGS. 12a-e. The proposed tRF (FIG. 12e) fixed the topology violations ($T_n=0$) compared to the pRF model (FIG. 12a, $T_n=870$), model-fitting (FIG. 12b, $T_n=489$), smoothing (FIG. 12c, $T_n=842$), or registration (FIG. 12d, $T_n=953$). Besides, the tRF achieved the smallest fMRI fitting error (RMSE is 0.296), compared to pRF (0.300), model-fitting (0.335), smoothing (0.301), or registration method (0.305). The average results for the first twenty observers were also reported in the dataset. The tRF reduced the mean fitting error from the second-best method's 0.376 (pRF method) to 0.372, and the topology violations were reduced from 1234 (median value) to 0. Those results showed that the tRF not only reduced the topology violation (i.e., compatible with neurophysiology conclusions) but also improved/kept the fitting power.

TABLE 3

The $\bar{e}/T_n$ (fitness/topology) of different methods for the first three HCP observers.

| Observers | PRF | Model-Fitting | Smoothing | Registration | IRF |
|---|---|---|---|---|---|
| S1 | 0.300/870 | 0.335/489 | 0.301/842 | 0.305/953 | 0.296/0 |
| S2 | 0.252/1119 | 0.288/934 | 0.253/1126 | 0.287/1141 | 0.250/0 |
| S3 | 0.276/1194 | 0.296/808 | 0.276/1197 | 0.298/1082 | 0.273/0 |

Methods and Systems for Registering Sensory Maps

In an exemplary embodiment, a method is disclosed herein that registers sensory maps, as shown in FIGS. 13-18.

Summary

It is an important topic in vision science and neurobiology to identify and analyze visual areas of the human brain (i.e. the visual atlas). Retinotopic mapping with functional magnetic resonance imaging (fMRI), provides a non-invasive way to delineate the boundaries of the visual areas. It is known in neurophysiology that retinotopic mapping is locally diffeomorphic (i.e. smooth, differentiable, and invertible) within each local area. However, the decoded visual coordinates from fMRI retinotopic mapping studies are not diffeomorphic because of the low signal-noise ratio of fMRI. The non-diffeomorphic problem is more severe near the most important fovea region because the size of the neuronal receptive field is much smaller and the retinotopic organization is more complicated. As a result, it is unreliable to directly delineate the visual atlas from a single subject's retinotopy.

To get a better visual atlas, especially for the fovea, it is preferable to use more subjects and take advantage of the group average. However, individuals' visual regions are different in size, shape and even location. Directly averaging several individuals' retinotopic maps cannot improve the result. Indeed, there are lots of methods and packages to register cortical surfaces, e.g. FreeSurfer, FSL, and BrainSuite. These methods are designed for diffeomorphic cortical wrapping using anatomical scalar information (e.g. curvature, thickness) only.

There is an opportunity to use retinotopic maps to improve registration of cortical areas. First, unlike image registration where only scalar features are available, retinotopic mapping associates an estimated visual coordinate (although noisy) to each location of the visual cortex. Second, the quality of the estimated visual coordinates can be assessed with performance metrics, which can help emphasize high-quality locations and under-weight poor-quality locations. These features have been used to register retinotopic measurements to a template. The used algorithm morphs the subject's surface to fit template data and introduces several penalties to avoid overstretching. However, these penalties compromise registration accuracy.

There is a need to model retinotopic registration, especially the diffeomorphic constraint. Visual coordinate differences may be quantified after registration, e.g., with Euclidean distance. The question is how to define and quantify diffeomorphism. Diffeomorphism has been long discussed in geometry. The registration method is disclosed herein that applies the Beltrami coefficient, an important concept in quasiconformal geometry, to quantify the diffeomorphic condition and model the registration as a function optimization problem with constraints. The present registration method eliminates redundant registration limitations and ensures diffeomorphic result. Then the linear Beltrami solver is applied to solve the registration model. The present model may also adopt human-based landmarks as a rough/precise guideline to help registration. The method of the present disclosure improves the accuracy and robustness of retinotopic map registration A purpose of exemplary systems and methods is to generate diffeomorphic retinotopic maps and improve the accuracy of the retinotopic atlas from fMRI measurements through the development of a specifically designed registration procedure. In consideration of retinotopic mapping features, a quasiconformal geometry-based registration model is formed and solved with efficient numerical methods. An exemplary registration method was compared with existing methods on synthetic data. The results demonstrate that it is superior to conventional methods for the registration of retinotopic maps. The application of an exemplary method to a real retinotopic mapping dataset also reduces registration errors.

Problem Restatement

Retinotopic Mapping

Figure 13:
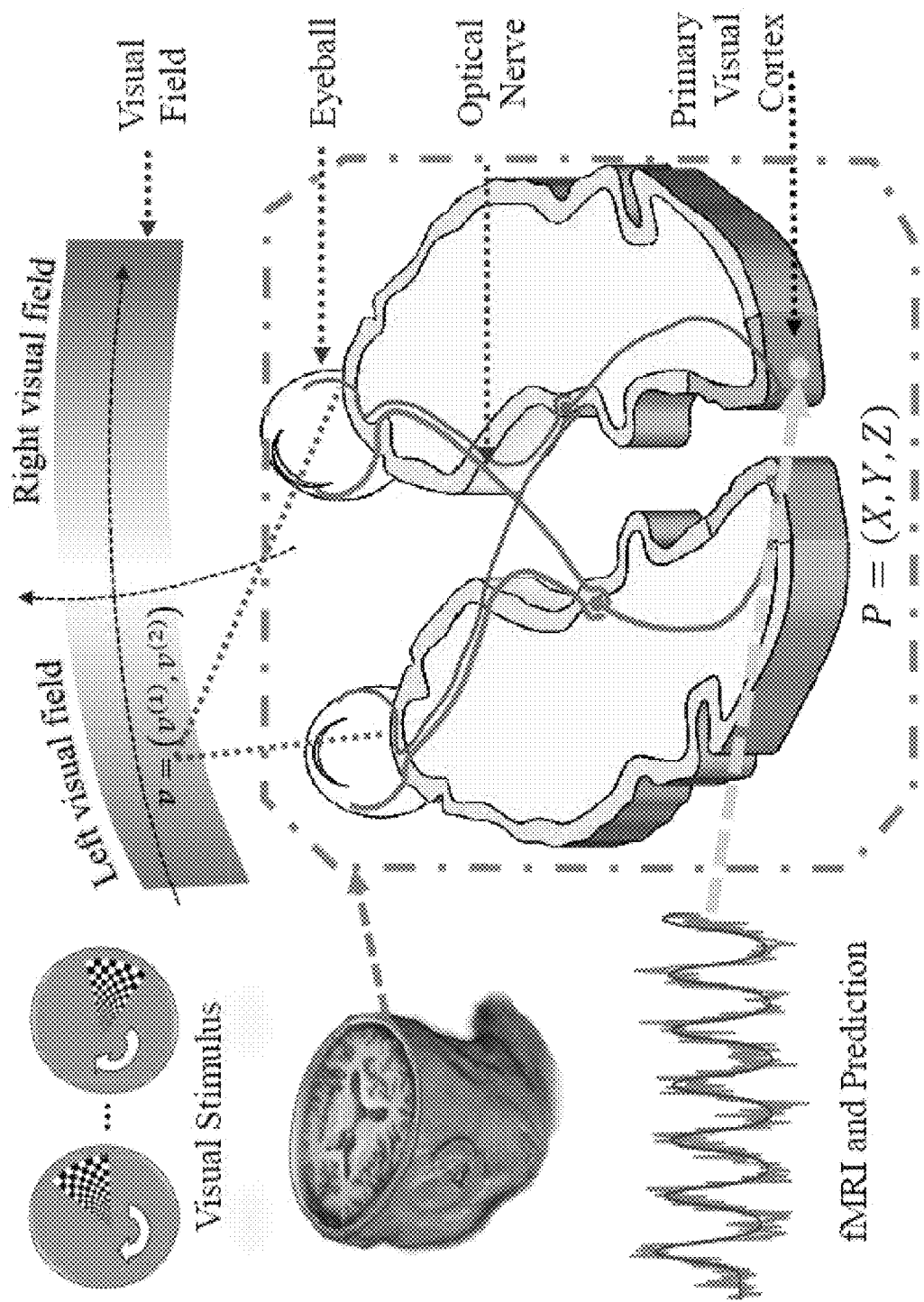
FIG. 13 illustrates the visual system in accordance with various exemplary embodiments.

The idea of retinotopic mapping via fMRI is briefly introduced here. Assume a unit illumination light spot is on point $v=(v^{(1)}, v^{(2)})\in \mathbb{R}^2$ in the visual field, as shown in FIG. 13. After the visual system's processing, the light spot will eventually activate a population of neurons. The main purpose of retinotopic mapping is to find, the center v and the extent $\sigma \in \mathbb{R}^+$ of its receptive field on the retina, for each point $P=(X, Y, Z)\in \mathbb{R}^3$ on visual cortex.

fMRI provides a noninvasive way to determine v and $\sigma$ for P, based on the following procedure. (1) Design a stimulus time sequence s (t; v), such that the stimulus sequence is unique for every visual coordinate, i.e., $s(t; v_1) \neq s(t; v_2)$, $\forall v_1 \neq v_2$; (2) Present the stimulus sequence to an individual and record the fMRI signals from the visual cortex; (3) For each fMRI time sequence on a cortical location, y(t; P), determine the corresponding receptive field, including its central location v and its size $\sigma$ on the retina, that most-likely generated the fMRI signals. Specifically, given the neurons' spatial response $r(v'; v, \sigma)$ (a predefined model depicts of neural response around v) and the hemodynamic response function h(t) (a model of the time course of neural activation to a stimulus), the predicted fMRI signal can be written as:

$$\hat{y}(v,\sigma)=\beta(\int r(v';v,\sigma)s(t;v_x,v_y)dv')*h(t) \quad (16)$$

where, $\beta$ is a coefficient that converts the units of response to the unit of fMRI activation, and * is the convolution operator. Then the perceptive center v and perceptive field size $\sigma$ are estimated by minimizing the difference between predicted signal and measurement, $$(v, \sigma) = \underset{(v,\sigma)}{\operatorname{argmin}} \int |\hat{y}(v, \sigma) - y(t; P)|^2 dt, \quad (17)$$

The retinotopic mapping of the entire visual cortex is obtained when (v, $\sigma$) is solved for every point on the cortical surface. The goodness of the estimation for each location is inferred by the variance explained, $R^2=\int|\hat{y}-\bar{y}|^2 dt / \int|y-\underline{y}|^2 dt$

Mathematical Model

In practice, cortical surface S is usually represented by a set of vertices $P_S=\{P_1, P_2, \ldots, P_n\}=\{P_i\}$ and triangular faces $F_S=\{F_i\}$, denoted by $S_S=(F_S, P_S)$. The fMRI signal is decoded for each location on cortical surface $P_i \in P_S$ according to Eq. (17). The decoding process generates a raw visual coordinate $v_i$, perception size $\sigma$, and variance explained $R_i^2$ for each vertex $P_i$. $S=(F_S, P_S, v_S, \sigma_s, R_s^2)$ is used to denote the bundle data of cortical surface as well as the raw retinotopic measurements. Here the capitalized subscript is used to denote all data of a subject, e.g. $P_S$ means all the point collection of the subject, and lowercase subscript to denote data of a point, e.g. $P_i$ is for i-th point of the subject. If the visual coordinate $v_S$ is accurate, then the visual atlas is of high quality. However, $v_S$ is influenced by the fMRI signal-noise ratio, head movement, subject's behavior and so on.

The next question is how to assign a new visual coordinate 13, such that it is most likely inferred by the measurements from all the subjects' data. One approach is registering each subject to a presumed template or mathematical model and then assigning the registered template value to the subject. An exemplary approach is to find a registration method and a presumed template $T=(F_T, P_T, v_T, \sigma_T, R_T^2)$, such that T the overall registration cost from all subjects' data to the template is minimal, i.e., $T=\arg \min_T \Sigma_J R(T, S_J)$, where R is the registration cost between the template T and J-th subject's data $S_J$.

Figure 14:
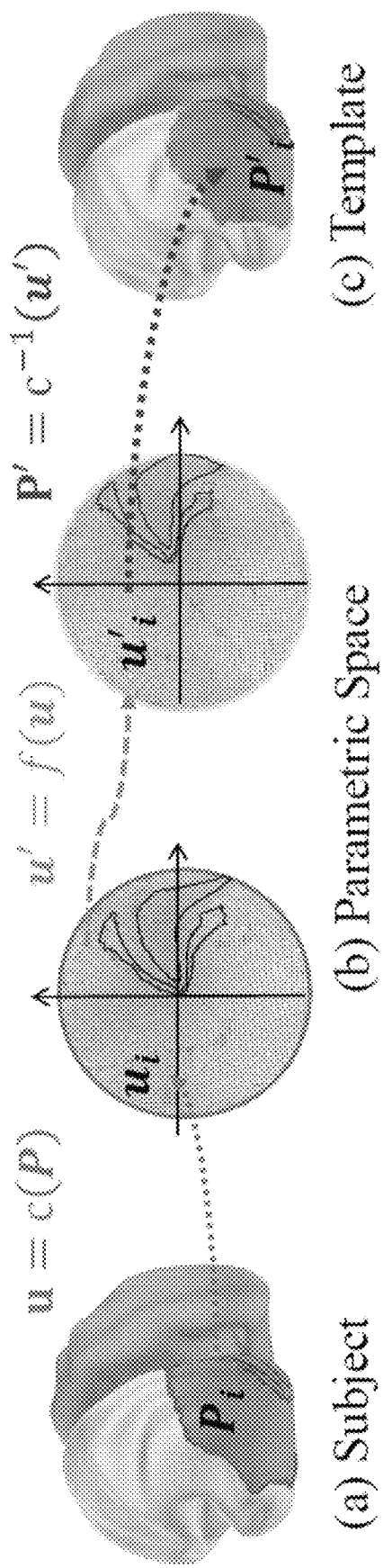
FIG. 14 illustrates several spaces and registration in accordance with various exemplary embodiments.
Figure 15:
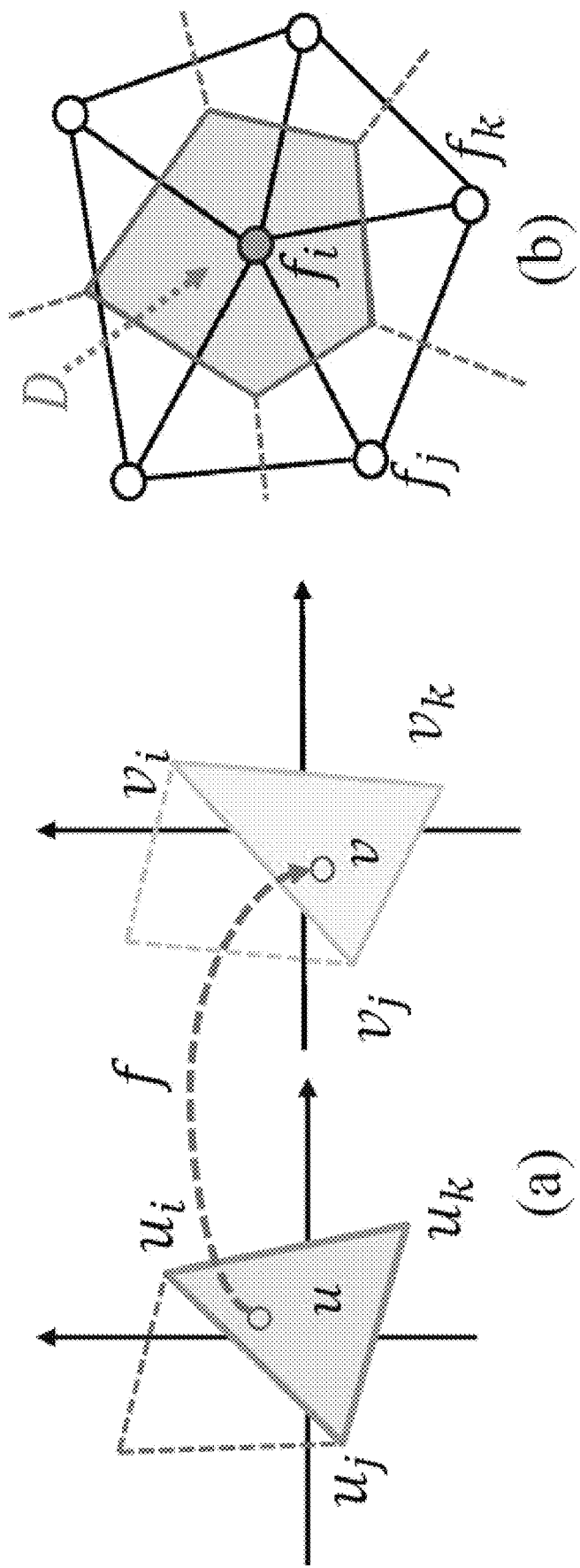
FIG. 15 illustrates (a) approximate the mapping in discrete and (b) the divergence approximation on the vertex ring in accordance with various exemplary embodiments.
Figure 16:
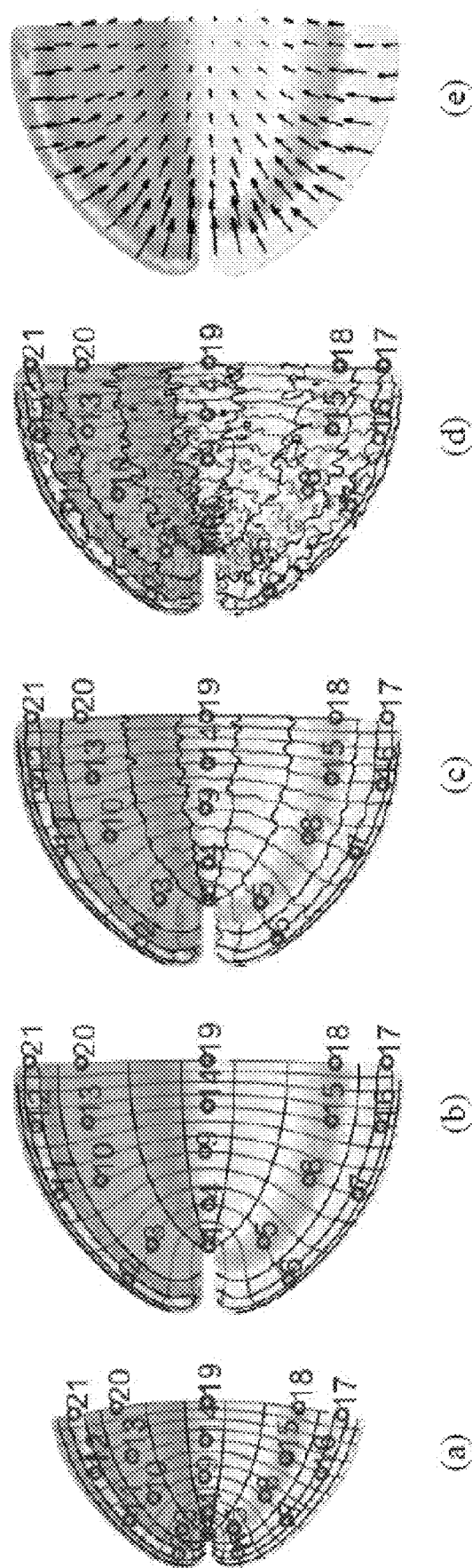
FIG. 16 illustrates template and subject in accordance with various exemplary embodiments: (a) template; (b) perfect subject; (c) subject data with a small added noise (Peak Signal-Noise Ratio is 20 dB); (d) Subject data with a big added noise (Peak Signal-Noise Ratio is 10 dB); (e) ground truth displacement (curves are for eccentricity/angle contour: landmarks are marked for (a)-(d))

A remaining problem may be to define the diffeomorphic registration function and its cost. It may be easy to understand the problems on 2D instead of the original 3D cortical surface. If a diffeomorphic function can be found from the cortical surface to a parametric domain, then the 3D registration can be simplified as a 2D problem, because the composite of two diffeomorphic functions is still diffeomorphic. A discrete conformal (angle preserving) mapping of the occipital region may be helpful. Specifically, as shown in FIG. 14 which is an illustration of several spaces and registration, a feature point is first defined that corresponds to the fovea as the center point. The geodesic distances from all vertices to the center point are calculated. Only the portion of cortical surface whose geodesic distance to the center point is within a certain value is considered, and this patch is mapped to a unit disk, c: $P \mapsto u$, $u=(u^{(1)}, u^{(2)})\in \mathbb{R}^2$.

Similarly, a similar portion of cortical surface is obtained and mapped to a parametric space, c': $P' \mapsto u'$, $u'=(u'^{(1)}, u'^{(2)})\in \mathbb{R}^2$ for template cortical surface (FIG. 14(c) gray color region). If a registration function $f: u \mapsto u'$ is found in the parametric space, the registration for the two cortical mesh as $P'=c^{-1} \cdot f \cdot c(P)$ can be obtained. Ideally, $f$ tries to: (1) minimize the retinotopic visual coordinate differences between the subject and the template, i.e. $\int w|v_S(f)-v_T|^2 du$ (w is proportional to the variance $R^2$); (2) ensure diffeomorphism; (3) introduces some smoothness. In geometry, diffeomorphism can be quantified by Jacobian, Beltrami coefficient, and so forth.

Beltrami coefficient is adopted to quantify the diffeomorphism, considering that Beltrami coefficient also quantifies angle deviation. Angle deviation is considered here because retinotopic mapping preserves angle to a considerable extent. Since cortical surface is conformal to visual space to some extent and cortical surface is mapped to the parametric space by conformal mapping, the registration $f$ should also preserve the angle to some extent. The Beltrami coefficient, associated with $f$ is defined as, $$\mu_f = \left(\frac{\partial f}{\partial u^{(1)}} + i\frac{\partial f}{\partial u^{(2)}}\right) / \left(\frac{\partial f}{\partial u^{(1)}} - i\frac{\partial f}{\partial u^{(2)}}\right). \quad (18)$$

If $|\mu_f|<1$ then $f$ is diffeomorphic. Considering the diffeomorphic condition, angle minimization, and smoothness requirements, the next is to seek $f$ minimizing the energy in Eq. (19), $$E=\int w|v_S(f)-v_T|^2+\lambda_1|\mu_f|^2+\lambda_2|\nabla f|^2 du. \quad (19)$$

Numerical Method

It is costly to minimize energy in Eq. (19) directly as it mixes Beltrami coefficient $\mu_f$ and mapping function $f$. An exemplary solution is to alternatively solve with respect to the mapping function and Beltrami coefficient in separate steps. Tools may be utilized to convert the mapping function and Beltrami coefficient back and forth.

Beltrami Coefficient

Given the explicit form of function $f$, it is possible to compute the Beltrami coefficient $\mu_f$ according to Eq. (18). In the discrete case, $f$ is interpreted linearly on each triangle. As shown in FIG. 15(a), for u within the triangle, $f(u)=\alpha_i v_i + \alpha_j v_j + \alpha_k v_k$, where $v_i=f_c(u_i)$, $v_j=f(u_j)$, and $v_k=f_c(u_k)$. The coefficients $\alpha_i, \alpha_j, \alpha_k$ are called the barycentric coefficients. Specifically, $\alpha_i$ (similarly for $\alpha_j$ and $\alpha_k$) is the area portion of triangle $\Delta uu_j u_k$ relative to $\Delta u_i u_j u_k$, i.e. $\alpha_i=\text{Area}(\Delta uu_j u_k)/$ Area($\Delta u_i u_j u_k$). Now it is possible to compute the Beltrami coefficient $\mu_{f_c}$ according to Eq. (18).

Linear Beltrami Solver (LBS)

The Linear Beltrami Solver (LBS) is introduced to recovery function $f=(f^{(1)}, f^{(2)})$ for the given Beltrami coefficient $\mu=\rho+i\tau$. According to the definition, i.e. Eq. (19), the following is obtained, $$\left(\frac{\partial f}{\partial u^{(1)}} + i\frac{\partial f}{\partial u^{(2)}}\right)\left(\frac{\partial f}{\partial u^{(1)}} - i\frac{\partial f}{\partial u^{(2)}}\right) = \rho + i\tau. \quad (20)$$

After reorganizing Eq. (20) and eliminating $f^{(2)}$, the following is derived, $$\nabla \cdot A \nabla f^{(1)} = 0, \quad (21)$$

where $$A = \begin{pmatrix} \alpha_1 & \alpha_2 \\ \alpha_2 & \alpha_3 \end{pmatrix}, \alpha_1 = \frac{(\rho-1)^2 + \tau^2}{1 - \rho^2 - \tau^2}, \alpha_2 = \frac{-2\tau}{1 - \rho^2 - \tau^2}$$

and $$\alpha_3 = \frac{1 + 2\rho + \rho^2 + \tau^2}{1 - \rho^2 - \tau^2}, \nabla f^{(1)} = (\partial f^{(1)}/\partial u^{(1)} + \partial f^{(1)}/\partial u^{(2)}),$$

and the divergence $\nabla \cdot$ on vector $G = A\nabla f^{(1)} = (G^{(1)}, G^{(2)})$ is defined as $$\nabla \cdot G = \partial G^{(1)}/\partial u^{(1)} + \frac{\partial G^{(2)}}{\partial u^{(2)}}.$$

By solving the partial equation Eq. (21) with certain boundary conditions, $f^{(1)}$ is solved. Similarly, $f^{(2)}$ is solved.

In the discrete case, gradient operator $\nabla f^{(1)}(u)$ can be written out with the linear interpretation. For discrete divergence $\nabla \cdot G$ operator, it is approximated on each vertex of its dual-cell (a cell includes neighboring triangles' circumcenters). In specific, as shown in FIG. 15(b), in consideration of the center vertex with its neighbors $N(u_i)$, the method of the present disclosure approximates $\nabla \cdot G(u_i)$ as the average of divergence on D, which is written as, $$\nabla \cdot G = \frac{1}{|D|}\int_{\partial D} G ds = \frac{1}{|D|}\sum_{T_j \in N(z_i)} G_{T_j} \cdot (u_k - u_j). \quad (22)$$

According to these approximations, there are a set of linear equations for $f_i$ and its neighbors. Finally, Eq. (21) is written in a matrix form and $f$ is solved efficiently.

Laplacian Smoothing and Chopping

Now it is possible to convert between the mapping function and Beltrami coefficient back and forth. During the registration, the smooth operation is applied to the function $f$ to make the registration smooth, namely the Laplacian smoothing. In specific, for a scalar function g, a smooth version of g' is obtained by solving the following equation, $$g' = \operatorname*{argmin}_{g} \int |\nabla g|^2 + \lambda \int |g - g'|^2, \quad (23)$$

where $\lambda$ is a constant. Eq. (23) can be efficiently solved by its Euler-Lagrange equation, i.e. $(-\nabla \cdot \nabla + 2\lambda I)v = 2\lambda\mu$. The smooth process is applied to $f^{(1)}$ and $f^{(2)}$, separately. For diffeomorphic mapping, the Beltrami coefficient $|\mu|<1$. Similarly, if there is a point whose $|\mu|>1$, the mapping is non-diffeomorphic. To pursue a diffeomorphic mapping, the present method shrinks the magnitude of |mu| and keeps the argument arg $\mu$ (notice $\mu$ is a complex function), i.e. $v'=v/|v|$, if $|v|>1$. This is called Chop.

Simple Registration Regardless Diffeomorphism

To use the features from retinotopic mapping, instead of updating the registration function using scalar features, the present method searches (by brute-force) retinotopic visual coordinates within the nearby cortical surface region $|f_i' - f_i| < r_0$, and updates the registration by, $$f_i' = \operatorname*{argmin}_{f_i'}(v_S(f_i') - v_T)^2, |f_i' - f_i| < r_0 \quad (24)$$

Algorithm

The overall registration process is summarized in the following Algorithm 4.

| Algorithm 4: Diffeomorphic Registration |
| --- |
| Input: Subject's data $S = (F_S, P_S, v_S, \sigma_S, R_s^2)$, template $T = (F_T, P_T, v_T, \sigma_T, R_T^2)$ and $\epsilon$ <br> Result: Registration function f <br> 1  begin <br> 2      Compute the conformal maps $u_S = c_s (F_S, P_S)$ and $u_T = c_T (F_T, P_T)$; <br> 3      Take Identical mapping as initial $u_T = f(u_T)$, ; <br>         repeat <br> 4         Update registration f' according to Eq. (24); <br> 5         Apply Laplacian smooth to f' <br> 6         Compute Beltrami coefficient v and Chop; <br> 7         Compute new mapping f' from v' by LBS; <br> 8      until max $|f' - f| < \epsilon$; <br> 9      return f <br> 10 end |

Results

Performance on Synthetic Data

Synthetic subject and template data in the scenario of retinotopic mapping are generated according to the double-sech model. The subject and template data are generated by two different sets of parameters, as shown FIGS. 16(a)-(e). The subject data is added with a small, as shown in FIG. 16(d), and big amount, as shown in FIG. 16(d), of uniform noise, respectively. The next step is to calculate the ground truth registration displacement from the subject to the template, as shown in FIG. 16(e). Then several methods are used to register the noisy subject data to the predefined template and get registration displacement. Eventually, the registration error (difference between method's registration displacement and ground truth displacement) is reported in the following Table 4.

The results indicate that: (1) an exemplary algorithm of the present disclosure achieves the smallest registration error and ensures diffeomorphism; (2) LDDMM and QCHR can also achieve almost diffeomorphic result, however, the method of the present disclosure is more precise; (3) TPS is fast, but its accuracy is poor; (4) LDDMM, D-Demos, and QCHR ensure diffeomorphism for image registration, however, they cannot guarantee overall diffeomorphism when the visual coordinates are considered as intensity of image;

and (5) Because of an alternative scheme in an exemplary method of the present disclosure, it usually takes approximately 100 to 150 seconds to register.

TABLE 4

Comparing registration performance relative to the ground truth.

| Method | Registration Error Mean | Registration Error Max | #Overlap Triangles | Time/(s) |
|---|---|---|---|---|
| TPS* [18] | 0.75/4.47 | 1.87/14.43 | 2/18 | 0.36 |
| Bayesian* [9] | 3.89/3.98 | 6.59/9.45 | 2079/2469 | 110 |
| D-Demos [19] | 1.12/1.20 | 2.34/2.59 | 2377/2473 | 1.6 |
| LDDMM [20] | 0.59/0.64 | 1.27/1.49 | 1/1 | 86 |
| QCHR* [11] | 0.06/0.10 | 0.62/0.47 | 1/0 | 173 |
| The Present Method* | 0.04/0.08 | 0.12/0.19 | 0/0 | 123 |

Results for small noise and big noise cases are reported respectively (Running time is reported in average).
Landmarks/anchors are given for methods with a "*" symbol.

HCP Data

Figure 17:
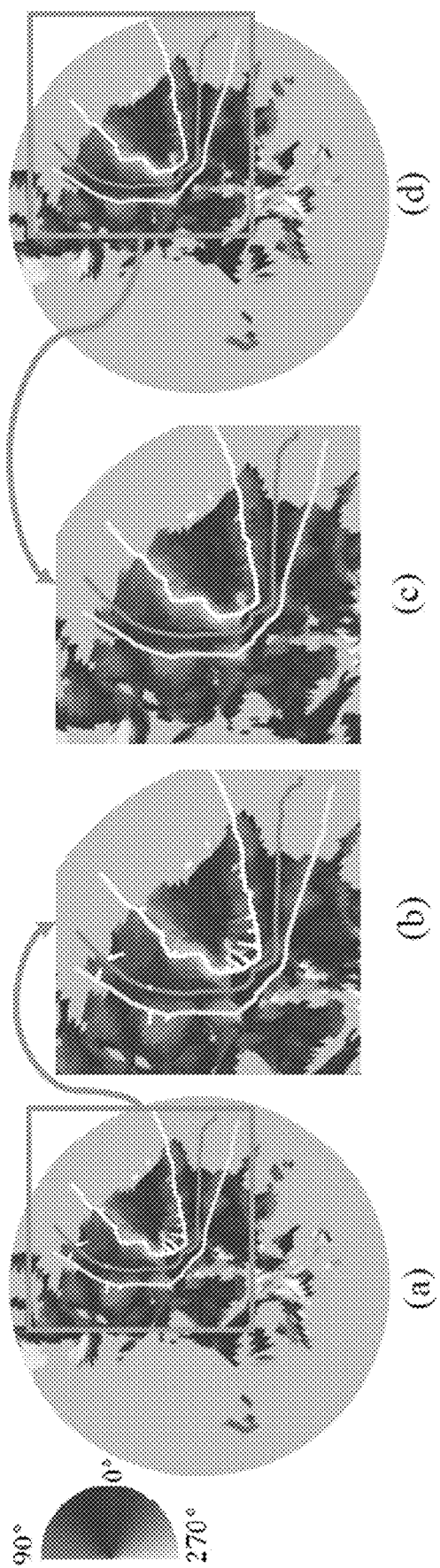
FIG. 17 illustrates: (a)-(b) Before and (c)-(d) After Registration of the left hemisphere of the subject '102816' in accordance with various exemplary embodiments.
Figure 18:
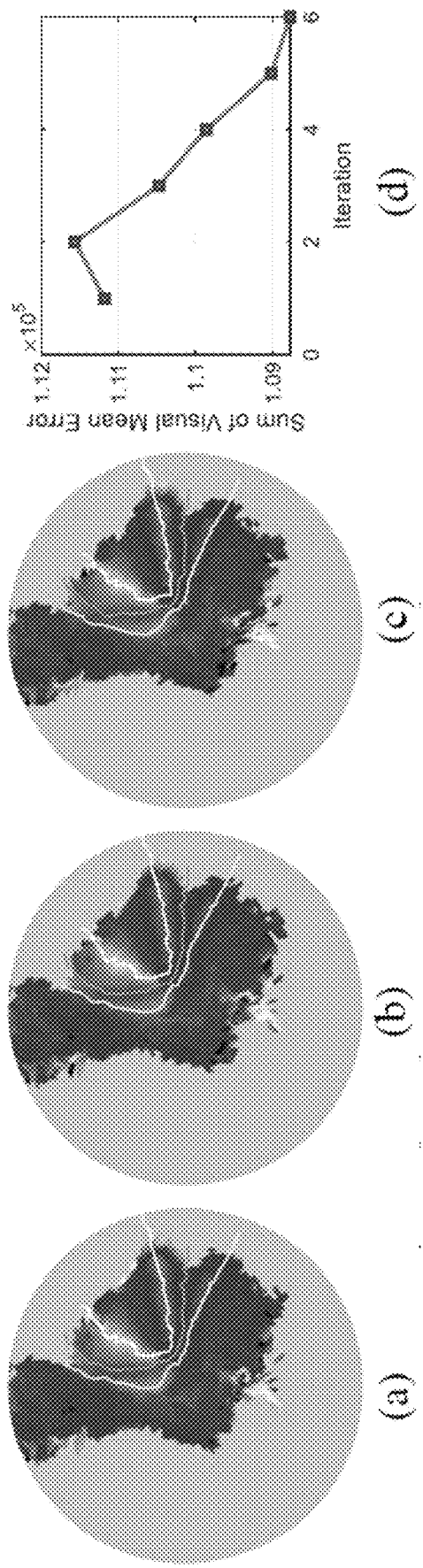
FIG. 18 illustrates the template morphing process in accordance with various exemplary embodiments.

A registration method of the present disclosure has been applied to the first twenty subjects of the Human Connectome Project (HCP) retinotopic dataset. The original retinotopic result is known. The first step of test is to initialize a template by averaging the subjects' data. Then, all subjects' data are registered to the initial template. FIG. 17 shows one subject's registration process. The curves are the boundaries of V1/V2/V3 inferred from the template. Before application of an exemplary registration method, as shown in FIGS. 17(a)-(b), the boundary is not aligned especially in the fovea region. FIGS. 17(a)-(b) result is from a registration result which used both the structural as well as some fMRI feature. FIGS. 17(c)-(d) illustrate results after application of an exemplary registration method. This means the alignment performed herein can further improve the result by incorporation of more retinotopic information.

Besides the subject registration, the overall registration cost is defined as the sum of visual coordinate error across subjects in the dataset. After registering all subjects' data, the average of the subjects is obtained and the same method to register the template is applied to the average data. This process is repeated until satisfactory results are obtained. FIG. 18(a)-(c) shows the first, second, and last iteration of the template, respectively. FIG. 18(d) shows the registration cost, overall visual error, is decreased during the process. The decreased overall visual error means the template is improved for human retinotopic maps. The registration method is also applicable in higher visual regions.

Sensory Mapping Method for a Human Brain

Figure 19:
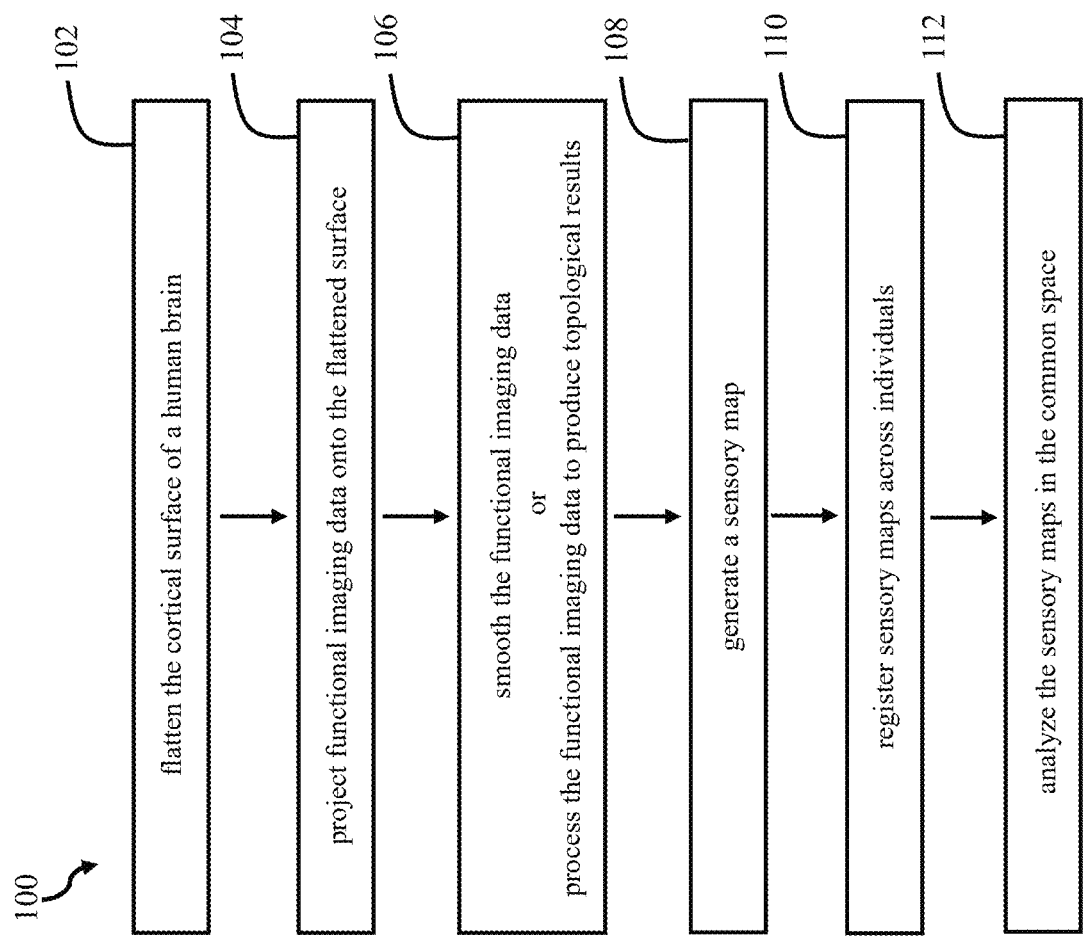
FIG. 19 illustrates a flow chart of a sensory mapping method for a human brain in accordance with various exemplary embodiments.

In various exemplary embodiments, a sensory mapping method 100 for a human brain is illustrated by the flow chart in FIG. 19. Method 100 comprises flattening the cortical surface of the human brain (step 102). In various embodiments, the flattening may comprise a conformal parametrization method. The flattening may comprise applying harmonic mapping to a unit disk and refining repetitively parametric coordinate for each point on a parameter domain to produce conformal mapping.

Method 100 further comprises projecting functional imaging data onto the flattened surface (step 104). Method 100 further comprises smoothing the functional imaging data or processing the functional imaging data to produce topological results (step 106). In various embodiments, the smoothing may comprise a topological smoothing method that utilizes a diffeomorphic smoother. In various embodiments, the smoothing may comprise applying Beltrami coefficient to quantify diffeomorphism and modeling the smoothing in an optimization framework.

In various embodiments, the processing may comprise a topology-preserving cortical surface segmentation method. In various embodiments, the processing may comprise segmenting the cortical surface of the human brain by preserving the prior connectivity pattern of the cortical surface areas, decoding the functional imaging data based on at least one topological condition within each cortical area, and repeating the segmentation and decoding.

In various embodiments, method 100 further comprises generating the sensory map (step 108). Method 100 may comprise registering sensory maps across individuals (step 110). In various embodiments, the registering may be diffeomorphic. In various embodiments, the registering may comprise a method that aligns a human brain sensory map of an individual to a predefined template. In some exemplary embodiments, method 100 comprises analyzing the maps in the common space (step 112).

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A sensory mapping method for a human brain, the method comprising:
   flattening a cortical surface of the human brain to form a flattened cortical surface, the flattened cortical surface comprising a two-dimensional surface;

projecting a functional magnetic resonance imaging (fMRI) data onto the flattened cortical surface;
smoothing, by a smoothing process, the functional magnetic resonance imaging (fMRI) data, the smoothing process comprising:
  determining retinotopic coordinates of each of a plurality of cortical areas based on the functional magnetic resonance imaging (fMRI) data;
  smoothing, by a diffeomorphic smoothing algorithm, the retinotopic coordinates of each of the plurality of cortical areas to form smoothed retinotopic coordinates of each of the plurality of cortical areas, wherein the diffeomorphic smoothing algorithm further comprises:
    computing a parametric coordinate for each of the plurality of cortical areas,
    performing Laplacian smoothing on the parametric coordinate for each of the plurality of cortical areas to form a smoothed retinotopic coordinate for each of the plurality of cortical areas,
    chopping the smoothed retinotopic coordinate for each of the plurality of cortical areas, and
    computing, by a Linear Beltrami Solver (LBS), a sensory map for each of the plurality of cortical areas; and
  repeating the diffeomorphic smoothing algorithm until a maximum absolute value of a Beltrami coefficient for the retinotopic coordinates of each of the plurality of cortical areas is less than one; and
responsive to the smoothing process, generating a diffeomorphic sensory map that corresponds to the sensory map where the maximum absolute value of the Beltrami coefficient for the retinotopic coordinates of each of the plurality of cortical areas is less than one.

2. The method of claim 1, wherein the flattening comprises:
  applying harmonic mapping to a unit disk; and
  refining repetitively the parametric coordinate for each point on a parameter domain to produce conformal mapping.

3. The method of claim 1, further comprising rendering the diffeomorphic sensory map with an image of stimuli that activate the cortical surface.

4. The method of claim 1, further comprising registering a plurality of sensory maps across a plurality of subjects.

5. The method of claim 4, wherein the registering is diffeomorphic.

6. A sensory mapping method for a human brain, the method comprising:
  flattening a cortical surface of the human brain to form a flattened cortical surface, the flattened cortical surface comprising a two-dimensional surface;
  processing a functional magnetic resonance imaging (fMRI) data to produce topological results, wherein the processing comprises:
    parameterizing the flattened cortical surface to a unit disk to form a parameterized cortical surface;
    computing, by a segmentation step, a topology preserving segmentation based on the parameterized cortical surface;
    decoding, by a decoding step, the functional magnetic resonance imaging (fMRI) data based on the topology preserving segmentation and the parameterized cortical surface to form a topological retinotopic map;
    repeating the segmentation step based on the topological retinotopic map and the decoding step until a theoretically guaranteed convergence occurs; and
  responsive to the processing, generating a diffeomorphic sensory map, the diffeomorphic sensory map corresponding to the topological retinotopic map after the theoretically guaranteed convergence occurs.

7. The method of claim 6, further comprising registering a plurality of sensory maps across a plurality of subjects.

8. The method of claim 7, wherein the registering is diffeomorphic.

9. The method of claim 7, wherein the registering comprises:
  applying a Beltrami coefficient to quantify diffeomorphism; and
  modeling the registering in an optimization framework.

* * * * *